United States Patent
Rouge et al.

(10) Patent No.: US 11,786,479 B2
(45) Date of Patent: *Oct. 17, 2023

(54) NUCLEIC ACID NANOCAPSULES FOR DRUG DELIVERY AND TARGETED GENE KNOCKDOWN

(71) Applicant: University of Connecticut, Farmington, CT (US)

(72) Inventors: Jessica Lynn Rouge, Farmington, CT (US); Joseph Awino, Farmington, CT (US)

(73) Assignee: UNIVERSITY OF CONNECTICUT, Farmington, CT (US)

(*) Notice: Subject to any disclaimer, the term of this patent is extended or adjusted under 35 U.S.C. 154(b) by 504 days.

This patent is subject to a terminal disclaimer.

(21) Appl. No.: 17/027,710

(22) Filed: Sep. 22, 2020

(65) Prior Publication Data

US 2021/0038528 A1 Feb. 11, 2021

Related U.S. Application Data

(62) Division of application No. 16/016,511, filed on Jun. 22, 2018, now Pat. No. 10,780,058.

(60) Provisional application No. 62/523,929, filed on Jun. 23, 2017.

(51) Int. Cl.
| | |
|---|---|
| *A61K 9/51* | (2006.01) |
| *A61K 47/69* | (2017.01) |
| *A61K 31/7088* | (2006.01) |
| *C07K 7/06* | (2006.01) |
| *C07K 7/08* | (2006.01) |
| *A61K 47/65* | (2017.01) |
| *C07K 5/10* | (2006.01) |
| *A61K 31/575* | (2006.01) |
| *A61K 31/4188* | (2006.01) |
| *A61K 31/355* | (2006.01) |

(52) U.S. Cl.
CPC ........ *A61K 9/5123* (2013.01); *A61K 31/7088* (2013.01); *A61K 47/65* (2017.08); *A61K 47/6929* (2017.08); *A61K 47/6935* (2017.08); *C07K 5/1002* (2013.01); *C07K 7/06* (2013.01); *C07K 7/08* (2013.01); *A61K 31/355* (2013.01); *A61K 31/4188* (2013.01); *A61K 31/575* (2013.01); *A61K 2300/00* (2013.01)

(58) Field of Classification Search
CPC ............... A61K 46/65; A61K 47/6929; A61K 47/6935; A61K 2300/00; C07K 7/06
USPC ...... 424/9.1; 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 8,790,621 B2 | 7/2014 | Zhao | |
| 10,780,058 B2* | 9/2020 | Rouge | ................ A61K 47/6929 |
| 2003/0124742 A1* | 7/2003 | Prakash | ................ A61K 47/65 |
| | | | 525/54.1 |
| 2014/0193342 A1* | 7/2014 | Giannneschi | ............ A61K 31/00 |
| | | | 424/78.22 |

OTHER PUBLICATIONS

Xu et al. "Esterase-catalyzed dePEGylation of pH-sensitive vesicles modified with cleavable PEG-lipid derivatives." J. Contol. Release. 2008, 130(3), p. 238-245.
Awino et al. "Nucleic Acid Nanocapsules for Enzyme-Triggered Drug Release." J. Am. Chem. Soc. 2017, 139(18), p. 6278-6281; Supportive information, p. 1S-10S.
Rouge et al. "Spherical Nucleic Acids as Divergent Platforms for Synthesizing RNA-Nanoparticle Conjugates through Enzymatic Ligation." ACS Nano. 2014, 8(9), p. 8837-8843.
Li et al. "Protection/Deprotection of Surface Activity and Its Applications in the Controlled Release of Liposomal Contents." Langmuir. 2012, 28(9), p. 4152-4159.
Zhao et al. "Surface-Cross-Linked Micelles as Multifunctionalized Organic Nanoparticles for Controlled Release, Light Harvesting, and Catalysis." Langmuir 2016, 32(23), p. 5703-5713.
Sel et al. "Effective prevention and therapy of experimental allergic asthma using a GAT A-3-specific DNAzyme," J. Allergy Clin. Immunol. 2008, 121(4), p. 910-916.
Krug et al. "Allergen-Induced Asthmatic Responses Modified by a GATA3-Specific DNAzyme," N. Engl. J. Med. 2015, 372, p. 1987-1995.
Hartmann et al. "Enzymatically Ligated DNA-Surfactants: Unmasking Hydrophobically Modified DNA for Intracellular Gene Regulation," ChemBioChem. 2018, 19(16), p. 1734.
Santiana et al. "Programmable Peptide-Cross-Linked Nucleic Acid Nanocapsules as a Modular Platform for Enzyme Specific Cargo Release," Bioconjugate Chem. 2017, 28(12), p. 2910-2914.
Shen et al. "Self-assemby of core-polyethylene glycol-lipid shell (CPLS) nanoparticles and their potential as drug delivery vehicles." Nanoscale. 2016, 8(31), p. 14821-14835.
International Search Report and Written Opinion for International Application No. PCT/US2018/039154.

* cited by examiner

*Primary Examiner* — Jane J Zara
(74) *Attorney, Agent, or Firm* — MCDONNELL BOEHNEN HULBERT & BERGHOFF LLP

(57) ABSTRACT

The present disclosure provides multifunctional nanoparticles. More particularly, the present disclosure relates to multifunctional nanoparticles having one or more of nucleic acid ligands; and methods of using such nanoparticles for treatment and/or diagnosis of diseases and conditions.

15 Claims, 13 Drawing Sheets
Specification includes a Sequence Listing.

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: AKH-anchor
<220> FEATURE:
<221> NAME/KEY: misc_structure
<222> LOCATION: (1)..(1)
<223> OTHER INFORMATION: SH

<400> SEQUENCE: 1
tttttttttt cacgtccagc ag                                             22

<210> SEQ ID NO 2
<211> LENGTH: 33
<212> TYPE: DNA
<213> ORGANISM: Artificial Sequence
<220> FEATURE:
<223> OTHER INFORMATION: GATA-3 DNAzyme
<220> FEATURE:
<221> NAME/KEY: misc_structure
<222> LOCATION: (1)..(1)
<223> OTHER INFORMATION: monophosphorylated site

<400> SEQUENCE: 2
gtggatggag gctagctaca acgagtcttg gag                                 33

<210> SEQ ID NO 3
<211> LENGTH: 24
<212> TYPE: DNA
<213> ORGANISM: Artificial Sequence
<220> FEATURE:
<223> OTHER INFORMATION: GATA-3 DNAzyme bridge

<400> SEQUENCE: 3
gcctccatcc acctgctgga cgtg                                           24

<210> SEQ ID NO 4
<211> LENGTH: 33
<212> TYPE: DNA
<213> ORGANISM: Artificial Sequence
<220> FEATURE:
<223> OTHER INFORMATION: Mutated DNAzyme
<220> FEATURE:
<221> NAME/KEY: misc_structure
```

```
<222> LOCATION: (1)..(1)
<223> OTHER INFORMATION: monophosphorylated site

<400> SEQUENCE: 4
gcggctggag gctagctaca acgagtctcg tag                                    33

<210> SEQ ID NO 5
<211> LENGTH: 24
<212> TYPE: DNA
<213> ORGANISM: Artificial Sequence
<220> FEATURE:
<223> OTHER INFORMATION: Mutated DNAzyme bridge

<400> SEQUENCE: 5
gcctccagcc gcctgctgga cgtg                                              24

<210> SEQ ID NO 6
<211> LENGTH: 19
<212> TYPE: RNA
<213> ORGANISM: Artificial Sequence
<220> FEATURE:
<223> OTHER INFORMATION: GATA-3 mRNA truncate 1
<220> FEATURE:
<221> NAME/KEY: misc_structure
<222> LOCATION: (1)..(1)
<223> OTHER INFORMATION: Cy3

<400> SEQUENCE: 6
cuccaagacg uccauccac                                                    19

<210> SEQ ID NO 7
<211> LENGTH: 19
<212> TYPE: RNA
<213> ORGANISM: Artificial Sequence
<220> FEATURE:
<223> OTHER INFORMATION: GATA-3 mRNA truncate 2
<220> FEATURE:
<221> NAME/KEY: misc_structure
<222> LOCATION: (1)..(1)
<223> OTHER INFORMATION: dye FAM
<220> FEATURE:
<221> NAME/KEY: misc_structure
<222> LOCATION: (19)..(19)
<223> OTHER INFORMATION: black hole quencher (BHQ)

<400> SEQUENCE: 7
cuccaagacg uccauccac                                                    19

<210> SEQ ID NO 8
<211> LENGTH: 6
<212> TYPE: PRT
<213> ORGANISM: Artificial Sequence
<220> FEATURE:
<223> OTHER INFORMATION: cathepsin B substrate

<400> SEQUENCE: 8

Cys Gly Phe Leu Gly Cys
1               5

<210> SEQ ID NO 9
<211> LENGTH: 14
<212> TYPE: PRT
<213> ORGANISM: Artificial Sequence
<220> FEATURE:
<223> OTHER INFORMATION: MMP9 substrate

<400> SEQUENCE: 9

Cys Gly Pro Leu Gly Leu Ala Gly Gly Glu Arg Asp Gly Cys
```

```
<210> SEQ ID NO 10
<211> LENGTH: 12
<212> TYPE: PRT
<213> ORGANISM: Artificial Sequence
<220> FEATURE:
<223> OTHER INFORMATION: peptide linker

<400> SEQUENCE: 10

Gly Pro Leu Gly Leu Ala Gly Gly Glu Arg Asp Gly
1               5                   10

<210> SEQ ID NO 11
<211> LENGTH: 4
<212> TYPE: PRT
<213> ORGANISM: Artificial Sequence
<220> FEATURE:
<223> OTHER INFORMATION: peptide linker

<400> SEQUENCE: 11

Gly Phe Leu Gly
1

<210> SEQ ID NO 12
<211> LENGTH: 8
<212> TYPE: PRT
<213> ORGANISM: Artificial Sequence
<220> FEATURE:
<223> OTHER INFORMATION: peptide linker

<400> SEQUENCE: 12

Gly Pro Met Gly Ile Ala Gly Gln
1               5
```

NUCLEIC ACID NANOCAPSULES FOR DRUG DELIVERY AND TARGETED GENE KNOCKDOWN

CROSS-REFERENCE TO RELATED APPLICATIONS

This application is a divisional application of U.S. patent application Ser. No. 16/016,511, filed Jun. 22, 2018, which claims the benefit of U.S. Provisional Patent Application No. 62/523,929, filed Jun. 23, 2017, both of which are incorporated herein by reference in their entireties.

REFERENCE TO AN ELECTRONIC SEQUENCE LISTING

A computer readable form of the Sequence Listing is filed with this application by electronic submission and is incorporated into this application by reference in its entirety. The Sequence Listing is contained in the file created on Oct. 29, 2020, having the file name "17-728-US-DIV_Sequence-Listing_ST25.txt" and is 4 kilobytes in size.

BACKGROUND OF THE INVENTION

Field of the Invention

The present disclosure provides multifunctional nanoparticles. More particularly, the present disclosure relates to multifunctional nanoparticles having one or more of nucleic acid ligands; and methods of using such nanoparticles for treatment and/or diagnosis of diseases and conditions.

Description of the Related Art

Nucleic acid-based therapeutics have become increasingly important drug candidates in recent years thanks to the advent of nanoparticle drug carriers. Such nucleic acids, including siRNA, antisense DNA, and catalytic nucleic acids have been shown to be effective tools for initiating intracellular gene regulation. However, these molecules suffer in their overall efficacy due to their inherent chemical instability. Recent studies have shown that the tight packing of nucleic acids at the surface of a nanoparticle can result in advantageous cellular delivery properties that the nucleic acid sequence alone cannot achieve. Such structures, referred to as spherical nucleic acids (SNAs) provide desirable delivery properties including increased cellular uptake through endocytosis and the prolonged half-life of nucleic acids. The later property is particularly important for the delivery of nucleic acids that rely on their folded structure to impart therapeutic effects including DNAzymes, ribozymes and aptamers.

Using such an SNA configuration on a colloidal gold nanoparticle scaffold, it was recently shown that a functional ribozyme could be successfully delivered into cells for regulating gene expression. However, as these structures were attached to inorganic nanoparticles (NPs), much of the particle core could not contribute to the overall therapeutic function other than to provide a scaffold on which to build the SNA configuration.

Therefore, there remains a need for assembling an SNA-like structure at the surface of a nanomaterial that could be utilized as a drug carrier and as a scaffold for further RNA and DNA functionalization. Although there are numerous soft material based approaches to drug encapsulation, the specific challenge remains to develop a material that can be rapidly functionalized with nucleic acids and rapidly release a drug cargo. The particle could then impart enhanced uptake due to the properties of the SNA, coupled with gene knockdown potential and small molecule drug delivery in a single construct.

SUMMARY OF THE DISCLOSURE

One aspect of the disclosure provides multifunctional nanoparticles including one or more of nucleic acid ligands covalently attached to a particle including non-polymeric amphiphiles,
  wherein hydrophobic groups of the amphiphiles are arranged toward the particle interior, and
  wherein hydrophilic groups of the amphiphiles are at the particle surface and are crosslinked through a triazole, thioether, or alkenyl sulfide group with one or more linkers cleavable by one or more intracellular or extracellular release agents.

Another aspect of the disclosure provides conjugates including the multifunctional nanoparticle of the disclosure and at least one therapeutic agent or diagnostic agent, wherein the multifunctional nanoparticle encapsulates the therapeutic agent.

Also disclosed herein are pharmaceutical compositions of the multifunctional nanoparticles of the disclosure or the conjugates of the disclosure. Examples of such compositions include those having at least one pharmaceutically acceptable carrier, diluent, and/or excipient together with a multifunctional nanoparticle or a conjugate as described herein.

Another aspect of the disclosure provides methods of treating a disease or disorder, including administering to a subject in need thereof an effective amount of the conjugate of the disclosure, wherein the linker is cleavable by one or more intracellular or extracellular release agent present in the subject, thus releasing the therapeutic agent or diagnostic agent. For example, in some embodiments, the disease or disorder is cancer, infection (e.g., bacterial, viral, or parasitic), pain, asthma, inflammation, neurological disease or disorder (e.g., Alzheimer's disease, Parkinson's disease, etc.). In certain embodiments, the disease or disorder is asthma, inflammation (e.g., asthma-induced inflammation or chronic obstructive pulmonary disease (COPD)-induced inflammation), infection (e.g., lower respiratory infections), or cancer.

BRIEF DESCRIPTION OF THE DRAWINGS

The accompanying drawings are included to provide a further understanding of the methods and compositions of the disclosure, and are incorporated in and constitute a part of this specification. The drawings illustrate one or more embodiment(s) of the disclosure, and together with the description serve to explain the principles and operation of the disclosure.

DETAILED DESCRIPTION OF THE INVENTION

Figure 1:
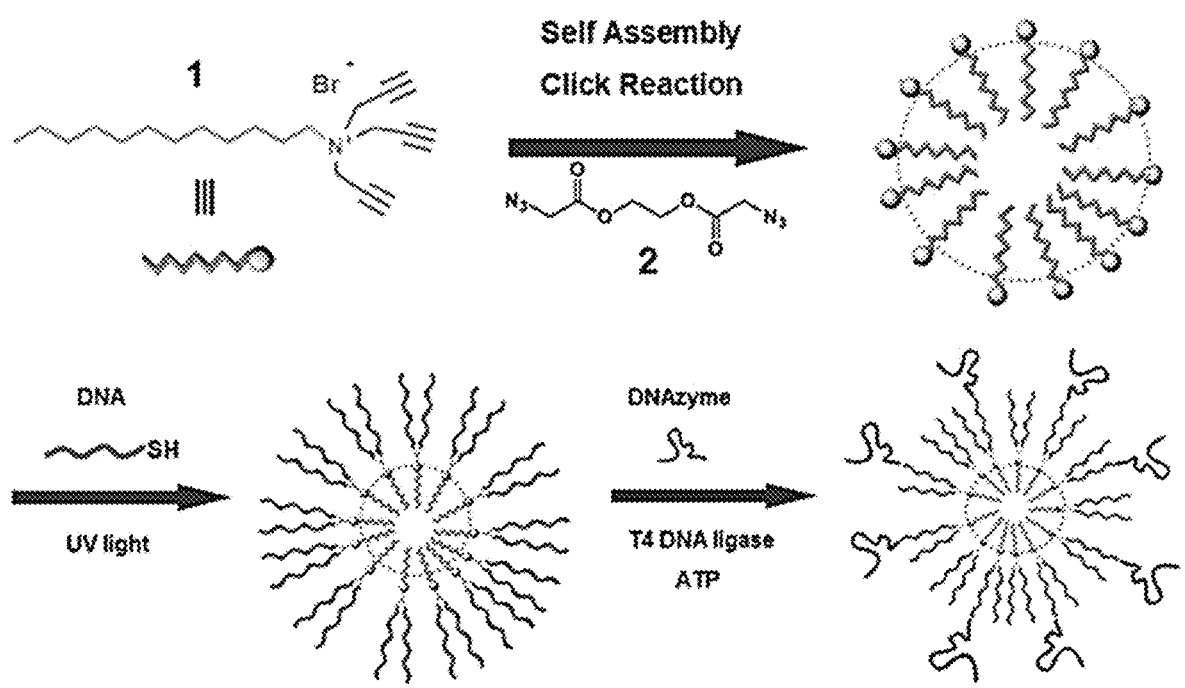
FIG. 1 shows a Stepwise assembly of nucleic acid nanocapsules. The trialkyl-modified surfactant 1 shown at top left is placed in water and quickly self-assembles into a micelle structure presenting alkynes at its surface. An esterified diazido cross-linker 2 is used to stabilize the structure using copper I catalyzed click chemistry. Remaining alkynes are used as a point of attachment for thiolated DNA molecules through a photodriven cross-linking step. After assembly of the NAN structure it can be further functionalized using an enzyme-mediated assembly approach with T4 DNA ligase to introduce DNAzymes to the NAN's surface.

Before the disclosed processes and materials are described, it is to be understood that the aspects described herein are not limited to specific embodiments, or examples, and as such can, of course, vary. It is also to be understood that the terminology used herein is for the purpose of describing particular aspects only and, unless specifically defined herein, is not intended to be limiting.

In view of the present disclosure, the methods and compositions described herein can be configured by the person of ordinary skill in the art to meet the desired need. In general, the disclosed materials and methods provide improvements in multifunctional nanoparticles (also referred herein as a nucleic acid nanocapsules or NANs or nanocapsules). For example, the multifunctional nanoparticles of the disclosure as described herein are capable in encapsulating small molecule drugs or dyes or rapidly functionalized with therapeutic nucleic acid ligands (such as a DNAzyme or siRNA sequence). In addition, the multifunctional nanoparticles of the disclosure as described herein are capable of nucleic acid delivery and targeted gene knockdown. Unexpectedly, in certain embodiments, the multifunctional nanoparticles can degrade in the presence of release agents commonly found within a cell (e.g., peptidase, protease, or esterase), therefore enhancing its degradation after deployment in an enzyme-specific fashion. The benefits of the multifunctional nanoparticles of the disclosure as described herein address a number of current and important drug delivery hurdles present in the art, such as the ability to easily functionalize the surface of a drug delivery vehicle for therapeutic or targeting applications, biodegradability, and the capacity for combination therapy, as the interior can be loaded with one drug, and the surface modified with a separate therapeutic biomolecule. In certain embodiments, the multifunctional nanoparticle of the disclosure as described herein, are particularly applicable to the delivery of hydrophobic small molecule drugs in conjunction with therapeutic oligonucleotides (siRNA, antisense oligonucleotides, microRNA, aptamers, DNAzymes, Ribozymes, etc.) that are useful for intracellular gene knockdown and altering protein expression levels. For example, the multifunctional nanoparticles of the disclosure as described herein deliver camptothecin, a topoisomerase inhibitor and cancer drug, along with a DNAzyme specifically designed to target the cleavage of GATA-3 mRNA. GATA-3 is a transcription factor that plays an important role in inflammation pathways by initiating downstream TH1 and TH2 cell differentiation. Cleavage of mRNA can result in blocked protein translation. If the DNAzyme on the nanoparticle is designed to target and cleave the mRNA transcript that encodes for GATA-3, it could prevent its downstream expression and thus prevent the important upstream steps involved in inflammation responses. Here, the multifunctional nanoparticle of the disclosure conjugated to DNAzyme enabled cellular uptake of the DNAzyme and resulted in specific and persistent knockdown of a target gene (e.g., 60%) for several hours. The DNAzyme exhibited this activity without the use of traditional cationic transfection agents and further chemical modifications.

In certain embodiments, the multifunctional nanoparticles of the disclosure as described herein are modular in nature, which makes them an excellent drug delivery vehicle for a number of different drug cargos and drug-biomolecule combination therapies. The modular nature of the nanoparticles of the disclosure as described herein allows a second therapeutic ligand, such as a nucleic acid ligand that, for example, can elicit protein knockdown, to be covalently attached to the surface of the particle. The ease of mixing and matching cargo and nucleic acid ligands makes the nanoparticles attractive along with its biodegradability and nontoxic components.

The multifunctional nanoparticles of the disclosure as described herein, for example, may offer several advantages, such as the ability to mix and match the cleavable linkers and the nucleic acid linkers and/or discrete population size (e.g. about 20 nm in size). In certain embodiments, the multifunctional nanoparticles of the disclosure as described herein present little or no risk of dynamic exchange and loss of nucleic acid ligand because the nucleic acid ligand is covalently liked to the particle and/or the steric crowding of ligands slows degradation due to nuclease activity. In certain embodiments, the multifunctional nanoparticles of the disclosure as described herein are capable of differentiating local biochemical environment as a trigger for therapeutic agent or diagnostic agent release. A major hurdle for current nucleic acid delivery platforms is the endosomal escape, which is necessary for therapeutic oligonucleotides to be more effective in the cytosol of cells. Thus, in some embodiments, the degradation of certain nanoparticles of the disclosure as described herein results in modified therapeutic oligonucleotides (e.g., such as hydrophobically modified oligonucleotide) capable of escaping the endosomal compartments of the cell.

Thus, one aspect of the disclosure provides multifunctional nanoparticles including one or more of nucleic acid ligands covalently attached to a particle including non-polymeric amphiphiles,
wherein hydrophobic groups of the amphiphiles are arranged toward the particle interior, and
wherein hydrophilic groups of the amphiphiles are at the particle surface and are crosslinked through a triazole, thioether, or alkenyl sulfide group with one or more linkers cleavable by one or more intracellular or extracellular release agents.

As provided above, the multifunctional nanoparticles of the disclosure include particles having non-polymeric amphiphiles. As used herein, the term "non-polymeric" means a material that is not a polymer (i.e., a molecule composed of repeat units). The amphiphiles of the disclosure have hydrophobic groups arranged toward the particle interior, and hydrophilic groups are at the particle surface. In certain embodiments, the hydrophobic groups of the amphiphile as otherwise described herein include $C_6$-$C_{22}$ alkyl, $C_6$-$C_{22}$ alkenyl, or $C_6$-$C_{22}$ alkynyl group, each optionally substituted with halo, $C_1$-$C_4$ alkyl, $C_2$-$C_4$ alkenyl, $C_1$-$C_6$ alkoxy, or —CO($C_1$-$C_{22}$ alkyl). In other embodiments, the hydrophobic groups of the amphiphile include unsubstituted $C_6$-$C_{22}$ alkyl, $C_6$-$C_{22}$ alkenyl, or $C_6$-$C_{22}$ alkynyl group. In other embodiments, the hydrophobic groups of the amphiphile include unsubstituted $C_6$-$C_{22}$ alkyl; or unsubstituted $C_6$-$C_{20}$ alkyl; or unsubstituted $C_6$-$C_{18}$ alkyl; or unsubstituted $C_6$-$C_{15}$ alkyl; or unsubstituted $C_6$-$C_{12}$ alkyl; or unsubstituted $C_6$-$C_{10}$ alkyl; or unsubstituted $C_{10}$-$C_{22}$ alkyl; or unsubstituted $C_{10}$-$C_{20}$ alkyl; or unsubstituted $C_{10}$-$C_{18}$ alkyl; or unsubstituted $C_{10}$-$C_{15}$ alkyl; or unsubstituted $C_{12}$-$C_{22}$ alkyl; or unsubstituted $C_{12}$-$C_{20}$ alkyl; or unsubstituted $C_{12}$-$C_{18}$ alkyl; or unsubstituted $C_{12}$-$C_{15}$ alkyl. In other embodiments, the hydrophobic groups of the amphiphile include optionally substituted $C_{10}$ alkyl. In other embodiments, the hydrophobic groups of the amphiphile include unsubstituted $C_{10}$ alkyl. In certain embodiments, the hydrophilic groups of the amphiphile as otherwise described herein include an ammonium group The amphiphiles of the disclosure as otherwise described herein are crosslinked through a triazole, thioether, or alkenyl sulfide group with one or more linkers. In certain embodiments, amphiphiles of the disclosure as otherwise described herein are crosslinked through a triazole group. In certain embodiments, amphiphiles of the disclosure as otherwise described herein are crosslinked through a thioether group. In certain embodiments, amphiphiles of the disclosure as otherwise described herein are crosslinked through an alkenyl sulfide group. In certain embodiments, the triazole, thioether, or alkenyl sulfide crosslinking group results from a reaction of alkyne or alkene moiety on the hydrophilic group of the amphiphile (e.g., on the ammonium group) and an azide or thiol moiety on the linker. In one example, the triazole crosslinker results from a reaction of alkyne moiety on the hydrophilic group of the amphiphile (e.g., on the ammonium group) with an azide moiety on the linker. In one example, the alkenyl sulfide crosslinker results from a reaction of alkyne moiety on the hydrophilic group of the amphiphile (e.g., on the ammonium group) with a thiol moiety on the linker. In one example, the thioether crosslinker results from a reaction of alkene moiety on the hydrophilic group of the amphiphile (e.g., on the ammonium group) with a thiol moiety on the linker. In certain embodiments, the alkyne or alkene moiety on the hydrophilic group of the amphiphile of the disclosure as otherwise described herein is one or two of prop-2-ynyl or prop-2-enyl; one or two of prop-2-ynyl, or one or two of prop-2-enyl. In certain embodiments, the hydrophilic group is tri(prop-2-yn-1-yl) amino or triallylamino. In certain embodiments, the crosslinking group results from a reaction of prop-2-ynyl. In certain embodiments, the crosslinking group results from a reaction of diallylamino.

The hydrophilic groups of the amphiphiles of the disclosure as otherwise described herein are crosslinked with one or more linkers that are cleavable by one or more intracellular or extracellular release agents. For example, in one embodiment, the linker is cleavable by one or more enzymes, such as, but not limited to, peptidases, proteases, esterases, or elastases. In one embodiment, the linker is cleavable by an esterase. In certain embodiments, the linkers of the disclosure as otherwise described herein are cleavable by one intracellular or extracellular release agent. In certain embodiments, the linkers of the disclosure as otherwise described herein are cleavable by two or more intracellular or extracellular release agents (e.g., wherein the linker comprises two or more different chemical groups each cleavable by a different release agent).

In certain embodiments, the linkers of the disclosure as otherwise described herein include a peptide (for example, cleavable with a peptidase or protease), wherein the peptide is at least two amino acids long. In certain embodiments, the peptide is at least two amino acids long. In certain embodiments, at least three amino acids long. In certain embodiments, at least four amino acids long. In certain embodiments, the peptide is between two and twenty amino acids long; or between three and twenty amino acids long; or between four and twenty amino acids long. In some embodiments, the peptide linker comprises GPLGLAGGERDG (SEQ ID NO:10), GFLG (SEQ ID NO:11), GPMGIAGQ (SEQ ID NO:12), Phe-Leu, Val-Ala, Val-Cit, Val-Lys, Val-Arg, or Phe-Lys. In some embodiments, the peptide linker comprises GPLGLAGGERDG (SEQ ID NO:10), GFLG (SEQ ID NO:11), or GPMGIAGQ (SEQ ID NO:12). In some embodiments, the peptide linker is GPLGLAGGERDG (SEQ ID NO:10), GFLG (SEQ ID NO:11), GPMGIAGQ (SEQ ID NO:12), Phe-Leu, Val-Ala, Val-Cit, Val-Lys, Val-Arg, or Phe-Lys. In some embodiments, the peptide linker is GPLGLAGGERDG (SEQ ID NO:10), GFLG (SEQ ID NO:11), or GPMGIAGQ (SEQ ID NO:12). In some embodiments, the peptide linker as otherwise described herein comprises (or further comprises) two Cys groups (for example, at each end of the peptide linker, such that the sulfur on the peptide linker makes up thioether or alkenyl sulfide group crosslinking the hydrophilic group of the amphiphile and the linker).

In some embodiments, the linker of the disclosure as otherwise described herein comprises GPLGLAGGERDG (SEQ ID NO:10) or GFLG (SEQ ID NO:11). In some embodiments, the linker of the disclosure as otherwise described herein is GPLGLAGGERDG (SEQ ID NO:10) or GFLG (SEQ ID NO:11).

In certain embodiments, the linkers of the disclosure as otherwise described herein include one or more of ester groups (for example, cleavable with an esterase). In one embodiment, the linkers of the disclosure as otherwise described herein include

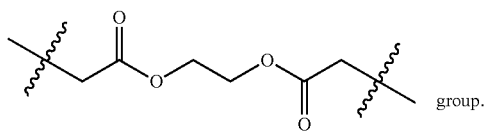 [SMILES: *CC(=O)OCCOC(=O)C*]
group.

group.

In certain embodiments, the linkers of the disclosure as otherwise described herein include one or more of hydrazone, semicarbazone, thiosemicarbazone, cis-aconitic amide, orthoester, acetal, ketal, or thioether groups, or a combination thereof, or other acid-labile groups that are hydrolyzable in the lysosome.

In certain embodiments, the linkers of the disclosure as otherwise described herein include at least two groups selected from an ester, hydrazone, semicarbazone, thiosemicarbazone, cis-aconitic amide, orthoester, acetal, ketal, thioether, disulfide, and a peptide, wherein the peptide is at least two amino acids long, or at least three amino acids long, or at least four amino acids long; or the peptide is between two and twenty amino acids long. In certain embodiments, the linker is cleavable by two or more intracellular or extracellular release agents and include at least two groups selected from an ester, hydrazone, semicarbazone, thiosemicarbazone, cis-aconitic amide, orthoester, acetal, ketal, thioether, disulfide, and a peptide as described herein.

In certain embodiments, the linkers of the disclosure as otherwise described herein include a disulfide group.

In certain embodiments, the linkers of the disclosure as otherwise described herein exclude disulfide group or another group cleavable under reducing conditions.

In certain embodiments, the non-polymeric amphiphiles of the disclosure as otherwise described herein are derived from

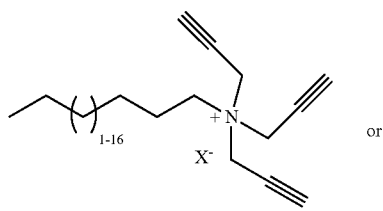

-continued

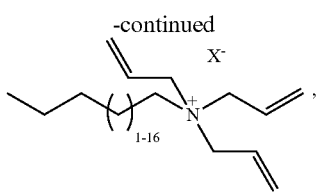

wherein X is halogen (e.g., Br). For example, in certain embodiments, the non-polymeric amphiphiles are derived from

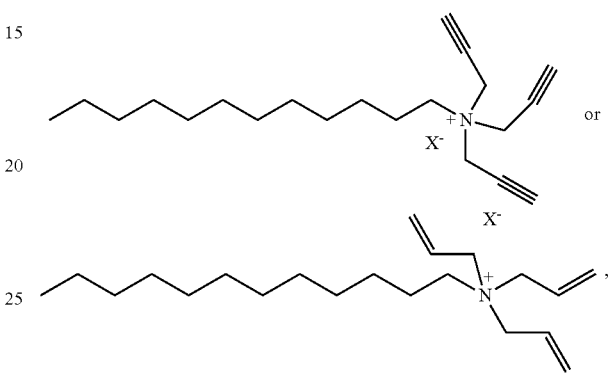

wherein X is halogen (e.g., Br).

As provided above, the multifunctional nanoparticles of the disclosure include one or more nucleic acid ligands covalently attached to the particle as otherwise described herein. For example, in some embodiments, the nucleic acid ligands of the disclosure are capable of selectively binding to a cell surface antigen (aptamer).

In some embodiments, the nucleic acid ligands of the disclosure are capable of selectively binding to a protein or a carbohydrate. In some embodiments, the nucleic acid ligands of the disclosure are capable of selectively binding to a protein, wherein the protein is selected from the group consisting of tumor-markers, integrins, cell surface receptors, transmembrane proteins, ion channels, membrane transport protein, enzymes, antibodies, and chimeric proteins. In some embodiments, the nucleic acid ligands of the disclosure are capable of selectively binding to a carbohydrate, wherein the carbohydrate is selected from the group consisting of glycoproteins, sugar residues, and glycocalyx.

In certain embodiments, the nucleic acid ligands of the disclosure as otherwise described herein are capable of selectively binding DNA, RNA, modified DNA, modified RNA, DNAzymes, ribozymes, mRNA, siRNA, microRNA, shRNA, and combinations thereof.

In certain embodiments, the nucleic acid ligands of the disclosure as otherwise described herein are capable of selectively binding to a cell during a specific developmental stage (e.g., stage having developmentally specific cell surface antigens) or to a cell in a specific disease state (e.g., a tumor cell that has tumor-associated antigens or tumor-specific antigens.)

In certain embodiments, the nucleic acid ligands of the disclosure as otherwise described herein are capable of gene regulation. For example, in some embodiments, the nucleic acid ligands capable of gene regulation can be siRNA, DNAzyme, ribozyme, microRNA, or any other therapeutic oligonucleotides (including antisense oligonucleotides).

In certain embodiments, the nucleic acid ligands of the disclosure as otherwise described herein can be native or modified, including phosphorthioated backbones, and 2' prime protected ribonucleic acids, or can be an aptamer, either RNA or DNA, modified or unmodified.

The inventors have recognized that, in certain embodiments, the multifunctional nanoparticle of the disclosure can transport the nucleic acid ligand to the cytosol. Without being bound by a particular theory, it is believed that the nucleic acid ligand may be assisted in its ability to reach the cytosol due to its covalent attachment to the amphiphiles (i.e., its relationship to the particle's hydrophobic group of the amphiphiles).

As provided above, the nucleic acid ligands of the disclosure are covalently attached to the hydrophilic groups of the amphiphiles. In certain embodiments, up to two nucleic acid molecules are attached to the hydrophilic groups of the amphiphiles (e.g., up to two per alkyne). In certain embodiments, one nucleic acid molecule is attached to the hydrophilic groups of the amphiphiles. In certain embodiments, two nucleic acid molecules are attached to the hydrophilic groups of the amphiphiles.

The nucleic acid ligands, for example in certain embodiments, are covalently attached to the hydrophilic groups of the amphiphiles through a thioether or alkenyl sulfide group. Such thioether or alkenyl sulfide groups may result from a reaction of alkyne or alkene moiety on the hydrophilic group of the amphiphile (e.g., on the ammonium group) and a thiol moiety (e.g., Cys) on the nucleic acid ligand. In certain embodiments, the alkyne or alkene moiety on the hydrophilic groups of the amphiphiles is prop-2-ynyl or prop-2-enyl, or prop-2-ynyl, or prop-2-enyl; or the alkyne or alkene moiety on the hydrophobic group of the amphiphile is prop-2-yn-1-ylamino or allylamino.

The multifunctional nanoparticles as described herein can be provided in a variety of different particle sizes, depending, e.g., on the amphiphiles and crosslinkers used for making them. For example, in certain embodiments, the multifunctional nanoparticle as described herein has a particle size within the range of about 0.1 nm to about 1 µm in diameter, e.g., 1 nm to 500 nm, or 1 nm to 100 nm, or 1 nm to 50 nm, or 1 nm to 30 nm, or 1 nm to 20 nm, or 1 nm to 10 nm, or 10 nm to 1 µm, or 10 nm to 500 nm, or 10 nm to 100 nm, or 10 nm to 50 nm, or 10 nm to 30 nm, or 10 nm to 20 nm, or 20 nm to 500 nm, or 20 nm to 100 nm, or 20 nm to 50 nm, or 20 nm to 40 nm, or 50 nm to 500 nm, or 50 nm to 100 nm in diameter. In certain embodiments, the multifunctional nanoparticle as described herein has a particle size within the range of about 10 nm to about 100 nm in diameter. The person of ordinary skill in the art can, in view of the materials and methods described herein, provide a desired particle size to a multifunctional nanoparticle.

In certain embodiments, the multifunctional nanoparticles as described herein have a discrete particle size and are monodisperse (i.e., uniform).

Another aspect of the disclosure provides conjugates comprising the multifunctional nanoparticle of the disclosure as otherwise described herein and at least one therapeutic agent or diagnostic agent, wherein the multifunctional nanoparticle encapsulates the therapeutic agent.

In certain embodiments, the conjugate as otherwise described herein includes a therapeutic agent. The therapeutic agent may be a hydrophobic small molecule drug, such as, but not limited to, an anti-cancer agent, an antibiotic, an antiviral, an antiparasitic agent, an anticoagulant, an analgesic agent, an anesthetic agent, an ion channel potentiator, an ion channel inhibitor, an anti-inflammatory, a metallodrug, and any combination thereof. For example, in certain embodiments, the therapeutic agent is selected from camptothecin, doxorubicin, daunorubicin, vincristine, paclitaxel, neocarzinostatin, calicheamicin, cisplatin, carboplatin, oxaliplatin, satraplatin, picoplatin, lurtotecan, annamycin, docetaxel, tamoxifen, epirubicin, methotrexate, vinblastin, vincristin, topotecan, prednisone, prednisolone, and abt-737.

In certain embodiments, the conjugate as otherwise described herein includes a diagnostic agent. The diagnostic agent may be, for example, a fluorophore, a radiolabeled nucleotide, a radioisotope, biotin, tocopherol, cholesterol, a steroid, or a electron dense tag and a metal chelator.

In certain embodiments, the conjugate as otherwise described herein includes a therapeutic or a diagnostic agent in the amount ranging from 0.25% to 10%, relative to the concentration of the non-polymeric amphiphile. In certain embodiments, the therapeutic or the diagnostic agent is present in the amount from 1% to 5%, or from 1% to 4%, or from 1% to 3%, or from 1% to 2%, or from 2% to 5%, or from 2% to 4%, or from 2% to 3%, or about 2.5%, relative to the concentration of the non-polymeric amphiphile.

As a person of skill in the art will recognize, the multifunctional nanoparticles of the disclosure or the conjugates of the disclosure may be provided in a pharmaceutical composition. For example, the multifunctional nanoparticles of the disclosure or the conjugates of the disclosure may be provided together with at least one pharmaceutically acceptable carrier, diluent, and/or excipient. The exact nature of the carrier, excipient or diluent will depend upon the desired use for the nanoparticles or conjugates, and may range from being suitable or acceptable for veterinary uses to being suitable or acceptable for human use. The composition may optionally include one or more additional therapeutic agents and/or diagnostic agents as described herein.

Another aspect of the disclosure provides methods of treating a disease or disorder, including administering to a subject in need thereof an effective amount of the conjugate of the disclosure, wherein the linker is cleavable by one or more intracellular or extracellular release agent present in the subject, thus releasing the therapeutic agent or diagnostic agent.

For example, in some embodiments, the disease or disorder is cancer, infection (e.g., bacterial, viral, or parasitic), pain, asthma, inflammation, neurological disease or disorder (e.g., Alzheimer's disease, Parkinson's disease, etc.). In certain embodiments, the disease or disorder is asthma, inflammation (e.g., asthma-induced inflammation or chronic obstructive pulmonary disease (COPD)-induced inflammation), infection (e.g., lower respiratory infections), or cancer.

In certain embodiments of the methods of the disclosure, the conjugate comprises a therapeutic agent as described herein.

The linkers of the disclosure may be selectively cleaved. For example, in one embodiment, no more than about 20%, no more than about 15%, no more than about 10%, no more than about 5%, no more than about 3%, or no more than about 1% of the linker is cleaved in an extracellular environment. In another embodiment, no less than about 20%, no less than about 15%, no less than about 10%, no less than about 5%, no less than about 3%, or no less than about 1% of the linker is cleaved in an extracellular environment.

In certain embodiments of the methods of the disclosure, the release mechanism is an enzyme expressed by tumor cells.

In certain embodiments of the methods of the disclosure, the release agent is a lysosome agent, endosome agent, and/or caveolae agent.

Definitions

The following terms and expressions used herein have the indicated meanings.

Substituents are intended to be read "left to right" (i.e., the attachment is via the last portion of the name) unless a dash indicates otherwise. For example, $C_1$-$C_6$ alkoxycarbonyl and —C(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, and —$CH_2CH(CH_2CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "halo" or "halogen" as used herein, means —Cl, —Br, —I or —F.

Certain aspects of the disclosure are now explained further via the following non-limiting examples.

EXAMPLES

Example 1: Preparation and Evaluation of Ester-Crosslinked NANs

General Method: For the purposes of synthesis and spectroscopic analyses, methylene chloride, methanol, hexanes, tetrahydrofuran, dimethylformamide, acetonitrile, and ethyl acetate were of HPLC grade. All other reagents and solvents were of ACS-certified grade or higher, and were used as received from commercial suppliers. $^1$H and $^{13}$C NMR spectra were recorded on a Bruker DRX-300 spectrometer. Mass spectrometry analysis was recorded on a Sciex QSTAR Elite mass spectrometer.

Synthesis of Surfactant 1 (N,N,N-tri(prop-2-yn-1-yl)dodecan-1-aminium bromide)

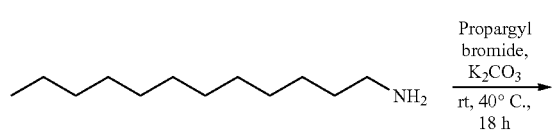

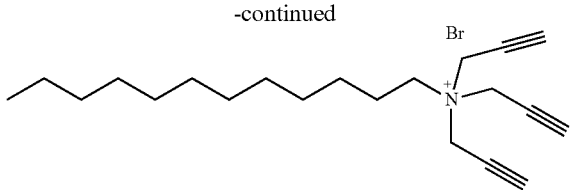

To a solution of dodecylamine (50 mg, 0.27 mmol) in 10 mL of methanol, anhydrous potassium bicarbonate (90 mg, 0.64 mmol) was added followed by dropwise addition of propargyl bromide (67 mg, 0.57 mmol) for a period of one minute. The mixture was stirred at room temperature for 12 hours after which propargyl bromide (34 mg, 0.29 mmol) was added and the solution stirred further at 40° C. for 6 hours. The mixture was cooled to room temperature and filtered. The solvents were removed from the filtrate and the concentrated sample purified by column chromatography over silica gel using methanol/methylene chloride (1:15) as eluent to yield the product as white powder (70 mg, 68%). $^1$H NMR (300 MHz, CDCl$_3$, δ): 4.80 (d, J=2.13 Hz, 6H), 3.7 (t, J=8.7 Hz, 2H), 3.04 (s, 3H), 2.01 (s, 2H), 1.40-1.20 (m, 18H), 0.9 (t, J=6.60 Hz, 3H). $^{13}$C NMR (300 MHz, CDCl$_3$, δ): 82.3, 83.3, 83.3, 69.8, 69.8, 69.8, 60.4, 49.9, 49.9, 49.9, 31.9, 29.7, 29.6, 29.4, 29.4, 29.3, 28.8, 26.2, 22.7, 22.4, 14.1. ESI-HRMS (m/z): [M-Br]+ calculated for $C_{21}H_{34}N$, 300.2691; found, 300.2664.

Synthesis of Ester-Crosslinked NAN:

In the typical procedure illustrated in FIG. 1, micelle solution of surfactant 1 (3.8 mg, 0.01 mmol) was prepared in Millipore water (1 mL). To the solution, ethane-1,2-diyl bis(2-azidoacetate) (diazide crosslinker 2; 2.8 mg, 0.012 mmol; prepared as described in Chen et al. *Synth. Commun.* 1998, 28, 3097), THPTA-Cu complex (0.00025 mmol), and sodium ascorbate (5.0 µL of a 99 mg/mL solution in water, 0.0025 mmol) were added. The reaction mixture was stirred slowly at room temperature. After 4 hours, the sample was purified by Sephadex G-25 Nap-5 column and the fractions containing crosslinked micelles (CM) were analyzed by UV-Vis, dynamic light scattering (DLS, and zeta potential. In a disposable cuvette, a solution containing the crosslinked micelles (10 µM) was prepared. To this solution, DNA anchor (30 µM) and 2-hydroxy-4-(2-hydroxyethoxy)-2-methylpropiophenone (2.5 µM) were added for a total volume of 500 µL in Millipore water. The mixture was placed in a Rhyonet reactor for 30 minutes. The thiol-yne photo-crosslinking was monitored by dynamic light scattering (DLS) and agarose gel electrophoresis.

Discussion:

The NAN's core is synthesized using a two-step approach combining self-assembly and a surface cross-linking step. The major difference in the NAN's core design is in the cross-linking step which can be used to trigger an enzymatic disassembly step, important for biochemically controlled drug release. First, an alkyne-terminated surfactant 1 was self-assembled in water. After assembly the particles are covalently cross-linked to hold the micelle-like structure intact. The cross-linker 2 is functionalized with azido groups on either end to facilitate cross-linking to the alkyne head groups presented by the surfactant. This cross-linker is incorporated into the particles design in order to stabilize the nanocapsule's core and recruit enzymes for initiating its degradation. Esterases are enzymes that can rapidly recognize and cleave ester bonds and have been shown to be effective targets for catalyzing drug release from nanomaterials. In addition to stabilizing the particle with ester linkages the NANs gain the potential to release hydrophobic small molecules from their core in response to enzymes (FIG. 1).

Esterases were also specifically chosen as the biochemical trigger for degrading the nanocapsules as these enzymes are known to be concentrated inside cellular endosomes. As many drugs and therapeutic antisense oligonucleotides need to reach the cytosol to exert their therapeutic effect, it was of interest to release the contents of the NAN once inside the cell in order to increase the likelihood its contents would make it to the cytosol.

Through careful control over the stoichiometry of the diazido cross-linker relative to the total number of alkynes presented at the particle surface (1:1.2 respectively), enough alkynes could be left unreacted to allow for attachment of a thiolated nucleic acid in the second assembly step. Using this approach thiolated DNA was attached to the surface of the nanocapsule using UV irradiation (365 nm) and a water-soluble photoinitiator traditionally used in polymerization reactions.

Figure 2:
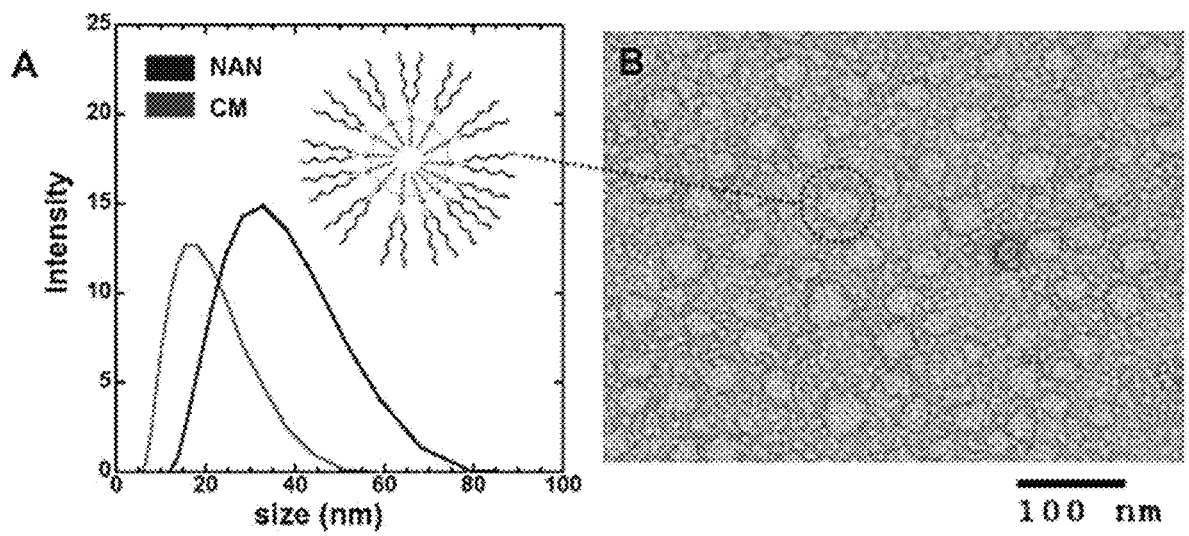
FIG. 2 illustrates characterization of NANs of Example 1 pre- and post-DNA assembly. (A) Dynamic light scattering measurements of particles prior to and after DNA conjugation, cross-linked micelle (CM) and NAN. (B) TEM micrograph showing the average size of uranyl acetate stained NANs.
Figure 3:
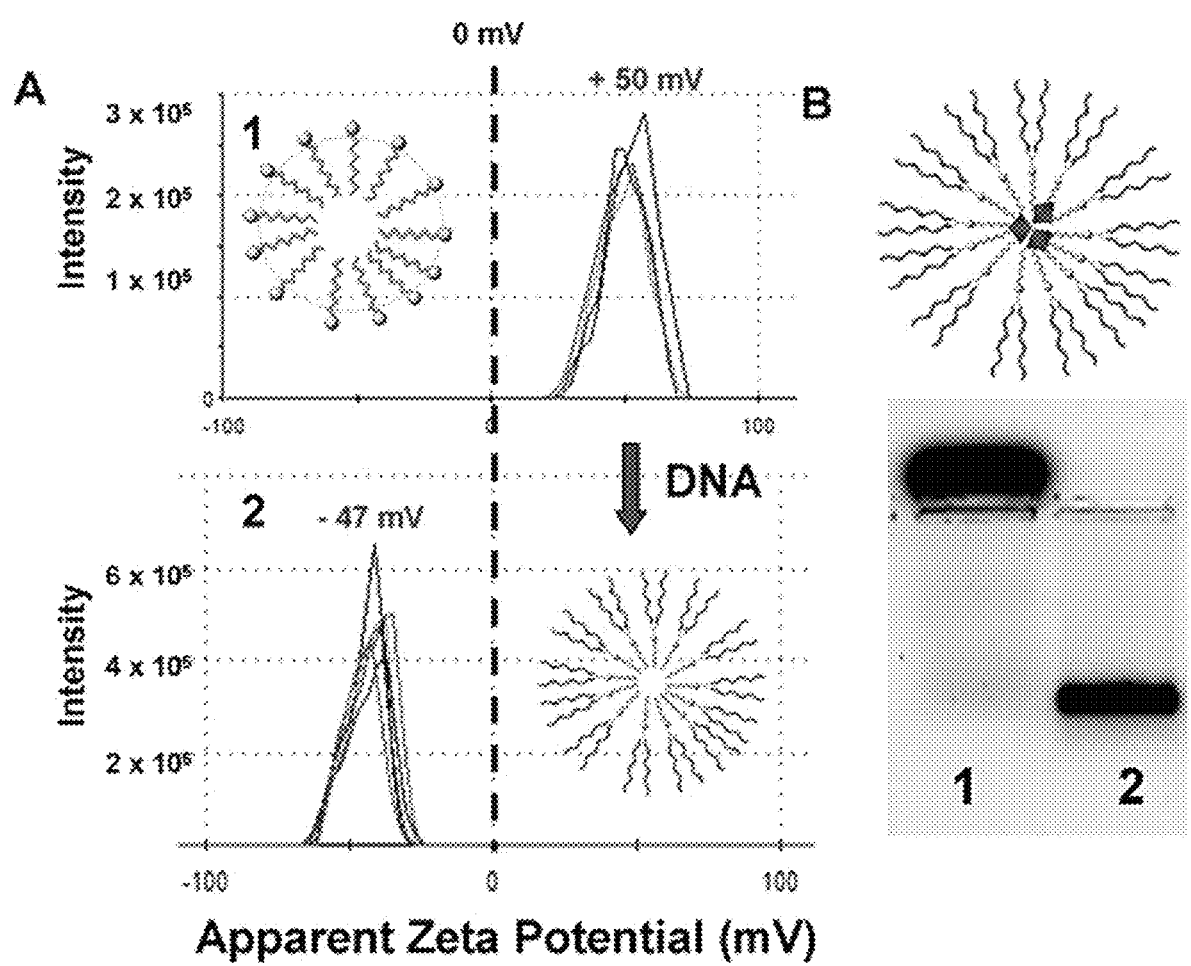
FIG. 3 illustrates characterization of NANs of Example 1 pre- and post-DNA assembly. (A) Zeta potential measurements of the nanocapsules pre and post functionalization with DNA. (B) 1% agarose gel showing movement of fluorescent NANs loaded with rhodamine B through an electric field post DNA functionalization (1, cross-linked micelle prior to DNA attachment; 2, NAN, post DNA attachment).

The resulting NAN is monitored during each step of assembly through a series of characterization techniques including dynamic light scattering (DLS), transmission electron microscopy (TEM) and zeta potential measurements (FIG. 2). The cross-linked micelle (CM) prior to DNA conjugation exhibited a uniform size distribution (20±3 nm) and positive charge (+50±4 mV). Such a positive surface charge was expected due to the presence of the tertiary amines presented by the alkyne functionalized headgroup. Post DNA attachment, the particles exhibited a dramatic shift in surface charge to −40 mV (FIG. 3A). The particle size also increased from 20 to 34 nm as would be expected for the attachment of a 22mer DNA strand (FIG. 2B). Additionally, post DNA functionalization, the once highly positively charged nanocapsule could now migrate through a 1% agarose gel under an electric field, indicative of the presence of the negatively charged DNA strands at the particles surface (FIG. 3B).

Figure 4:
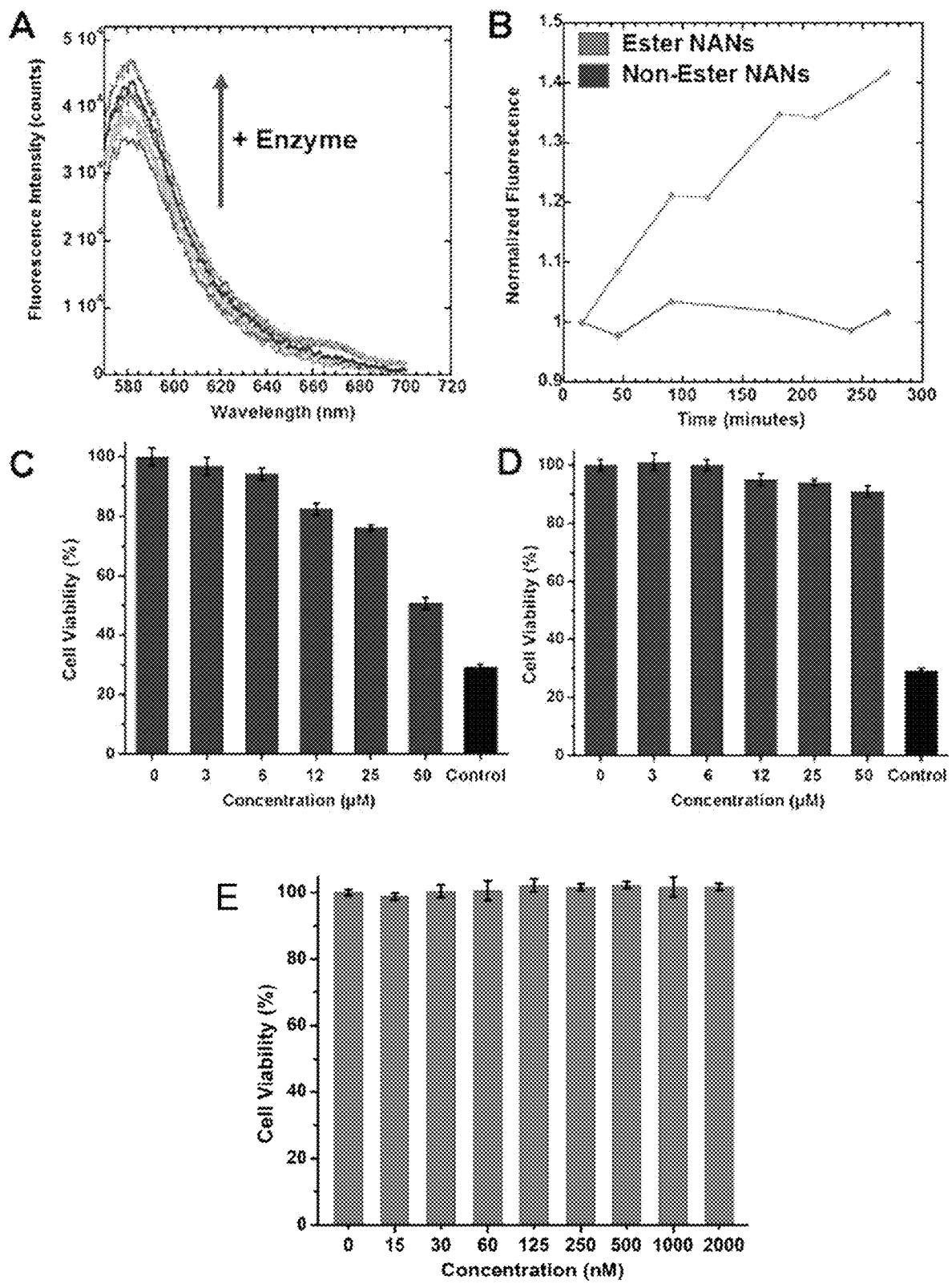
FIG. 4 illustrates enzyme-mediated release of internal cargo of NANs of Example 1. (A) Total emission in a sample of NANs cross-linked with compound 2 containing rhodamine B, post treatment with esterase over time in buffer. (B) Representative plots of ester-linked NANs and nonester-linked NANs (made with non-esterified crosslinker 3) versus time after 2 h of treatment with esterase. (C,D) Evaluation of cell toxicity in HeLa cells in the presence of NANs loaded with camptothecin. Results indicate a dose dependent decrease in cell viability post 24 h incubation with ester-linked NANs (dark gray bars) in (C), and a limited effect from NANs linked by a non-esterified linker (black bars) in (D). Concentrations indicate total camptothecin loaded within NANs. Control is 50 μM free drug. These results indicate that the release of the apoptotic drug is dependent upon the presence of both the esterified cross-linker and the esterase. (E) Cell viability tests of HeLa Cells incubated with increasing concentrations of NANs.

Evaluation of Release Ability:

To determine the ability of NANs to release a small molecule from its interior, NANs were synthesized in the presence of rhodamine B dye. The effective loading of the particles was optimized at 2.5% loading by concentration although loading as high as 10% was possible (results not shown). The resulting particles were then subjected to treatment with porcine liver esterase and monitored using fluorescence spectroscopy. In short, A solution of NANs (3 µM) was prepared in Tris HCl buffer in a total volume of 400 µl. The solution was placed into an external Peltier unit and allowed to come to 37° C. Esterase (Porcine liver esterase, Sigma Aldrich, 5 units) was added and a reading was taken immediately. All samples were excited at 545 nm and scanned between 570 and 700 nm using a Jobin Yvon Fluorometer while heated at 37° C. This process was repeated at 5, 15, 30, 45, 60, 90, 120, 180, 210, 240, 270, and 300 minutes. The NANs containing ester linkages were successfully cleaved as indicated by an increase in the samples fluorescence over time (FIG. 4A). As a control, a nanocapsule cross-linked with non-ester linkage was prepared by reacting surfactant 1 with 1,4-diazidobutane-2,3-diol (3). This nanocapsule cross-linked with non-ester linkage was treated with esterase and release of the dye was not observed (FIG. 4B). The lack of dye release indicates that the stability of the particle is gated by the enzymatic environment of the nanocapsule. The NANs were also evaluated for their cell toxicity effects and shown to be nontoxic up to micromolar concentrations (FIG. 4E).

Next, cells were incubated with the NANs to see if the SNA-like construct to determine cellular uptake without transfection agents, a feature exhibited by SNA configurations on nanoparticle surfaces. Confocal studies showed that the particles were indeed readily taken up by cells in a fashion similar to that seen with traditional SNA-like structures (see FIG. 5C-F), and were shown to colocalize within regions of the cell that indicate endocytosis as the main mechanism of uptake.

Example 2: Preparation of Drug-Loaded Ester-Crosslinked NANs

Ligation of DNAzyme/Mutated DNAzyme to Nucleic Acid Nanoparticle (NAN): 10 µM GATA-3 DNAzyme/mutated DNAzyme and 20 µM GATA-3 DNAzyme bridge/mutated DNAzyme bridge were added to 200 µL of 4 µM solution of NANs of Example 1 functionalized with anchor. Water was added to the sample to reach a total volume of 300 µL. The solution was heated at 70° C. for 10 minutes and cooled to room temperature. 5 mM ATP, 15 µL of 1 U/µL T4 DNA Ligase (Invitrogen), 1× ligase buffer were mixed. Water was added to this second solution to reach a total volume of 300 µL. Placed on 25° C. heat block for 2 hours, ligase was heat inactivated at 65° C. for 10 minutes.

TABLE 1

DNAzyme-NAN characterization and activity assays DNA and RNA sequences

| | |
|---|---|
| Anchor (AKH-anchor) | 5'-SH-TTT TTT TTT TCA CGT CCA GCA G-3' (SEQ ID NO: 1) |
| GATA-3 DNAzyme | ** 5'-GTG GAT GGA CCC TAG CTA CAA CGA CTC TTG GAG-3' (SEQ ID NO: 2) |
| GATA-3 DNAzyme bridge | 5'-GCC TCC ATC CAC CTG CTG GAC CTC-3' (SEQ ID NO: 3) |
| Mutated DNAzyme | *** * 5'-GCG GCT GGA CCC TAG CTA CAA CGA CTC * * TCG TAG-3' (SEQ ID NO: 4) |
| Mutated DNAzyme bridge | 5'- GCC TCC AGC CCC TGC TGG AC CTC-3' (SEQ ID NO: 5) |
| GATA-3 mRNA truncate 1 | 5'-Cy3-CUC CAA GAC GUC CAU CCA C-3' (SEQ ID NO: 6) |
| GATA-3 mRNA truncate 2 | 5' FAM- CUC CAA GAC GUC CAU CCA C - BHQ-13' (SEQ ID NO: 7) |

* indicates mutations,
** indicates monophosphorylated site.
Note:
mutations in DNAzyme affect the flanking region of the DNAzyme to test for target specificity. No changes were made to the catalytic loop region associated with cleavage.

Cleavage Assay. To test the activity of the GATA-3 DNAzyme, both free DNAzyme and 5 µM of ligated NANs were incubated with 0.5 µM GATA-3 mRNA truncate, both in the presence and absence of salts (10 mM MgCl$_2$ and 100 mM NaCl). The different reactions were then run on an 8% denaturing polyacrylamide gel at 350 V for 30 minutes. The gel was scanned using both a 473 nm laser and a 532 nm laser.

Cellular Uptake and Confocal Imaging of DNAyzme-NANs. HeLa cells were grown in 10% FBS in DMEM with 1% Penicillin/Streptomycin. Confluent cells were treated with 1 µM functionalized NANs for 3.5 hours, then washed with 1×PBS. Media was replaced and cells were imaged using a Leica SP8 confocal microscope.

Ligated DNAzyme and Fluorescent mRNA Probe Experiments. The interaction between ligated DNAzyme-NANs and a dually labeled black hole quencher (BHQ) and dye (FAM) labeled mRNA truncate was investigated using a Horiba Yvon flurolog-3 fluorometer.

A solution of $MgCl_2$ (10 mM), NaCl (100 mM), ligated DNAzyme NANs (100 nM) and di $H_2O$ was used as a control to determine the auto fluorescence from the NAN and salt solution. Prior to mixing, the ligated DNAzyme NAN was heated to 70° C. for ten minutes and then cooled to room temperature. The control sample was then held at 37° C. in a Horiba Jobin Yvon fluorometer using an external Cary single cell peltier accessory. The control sample was excited at 470 nm and scanned from 485 to 700 nm.

A second sample was prepared this time containing the BHQ FAM mRNA truncate. A solution of $MgCl_2$ (10 mM), NaCl (100 mM), ligated DNAzyme NAN (100 nM) and H2O was prepared as above, with the ligated DNAzyme NAN being heated to 70° C. for ten minutes prior to mixing. The sample was cooled to and held at 37° C. in the Horiba Jobin Yvon fluorometer using an external Cary single cell peltier accessory. The dually labeled BHQ-mRNA-FAM (10 nm, BioSearch Technologies) was added to the sample and a measurement was taken immediately. The sample was excited at 470 nm and scanned between 485 and 700 nm. Further measurements were taken at 2, 5, 10, 15, 20, 30, 45, 60 minutes.

Discussion:

The NANs of Example 1 were loaded with camptothecin, an apoptosis inducing drug and incubated with HeLa cells for 4 h at 37° C. Cell proliferation studies showed that cells treated with camptothecin-loaded NANs (50 µM drug) effectively limited the growth of cells by 50% relative to untreated cells. Non-ester cross-linked NANs loaded with 50 µM drug had minimal effect on cell growth (FIG. 4D).

A fully degradable aspect of the NAN construct was evaluated through the attachment of a DNAzyme that requires its folded structure to function in the cleavage of mRNA. The DNAzyme hgd40 was specifically chosen as a test oligonucleotide sequence as it has recently been shown to rapidly cleave mRNA encoding an important transcription factor (GATA-3) involved in inflammation pathways. In order to design this construct the DNAzyme was first enzymatically assembled onto the NANs surface using a recently developed enzyme ligation approach compatible with SNA like structures as described by Rouge et al. (ACS Nano 2014, 8, 8837).

Figure 5:
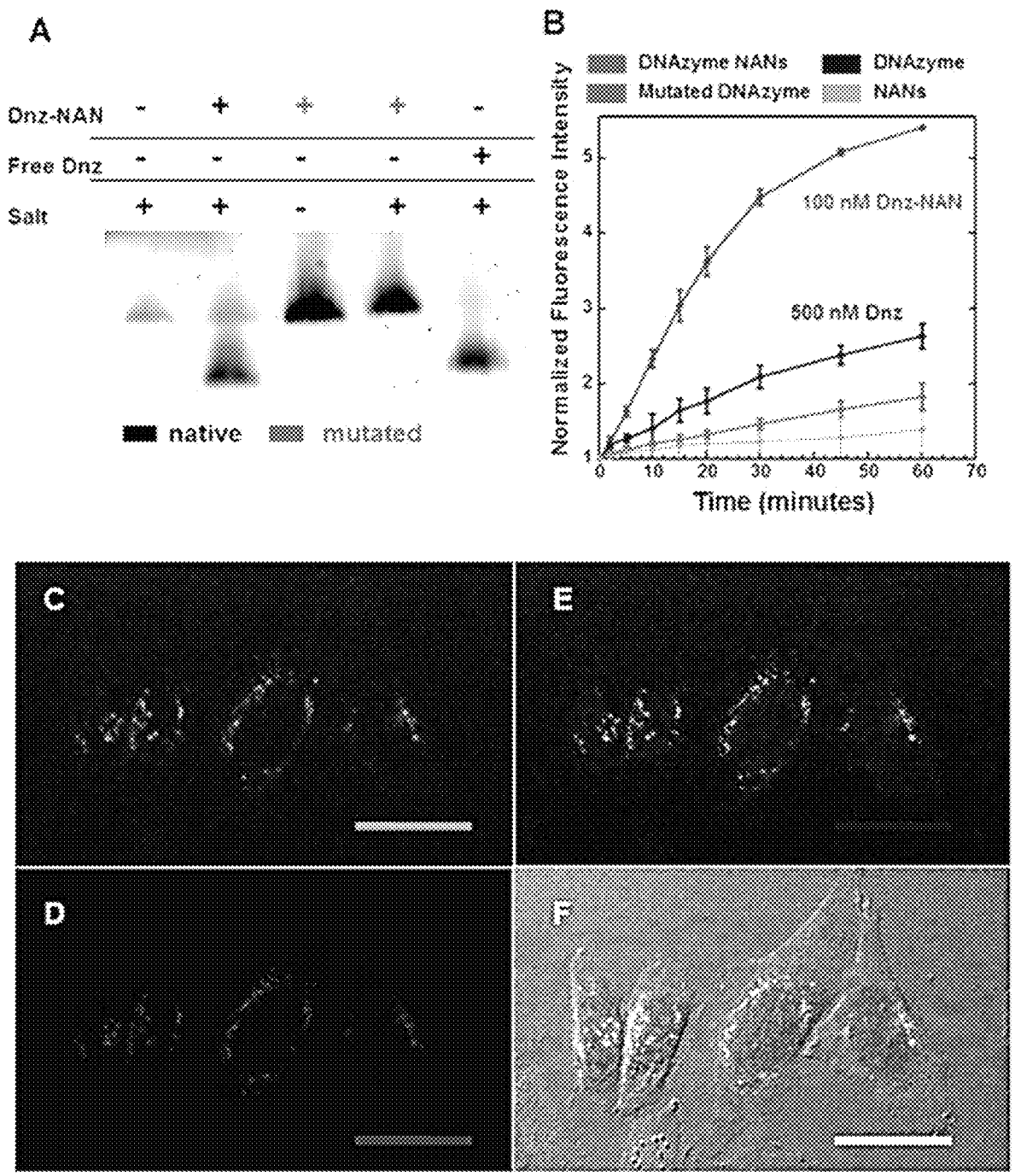
FIG. 5 shows cleavage of mRNA truncates using DNAzyme-functionalized NANs and cellular uptake. (A) Polyacrylamide gel electrophoresis showing the cleavage of RNA induced by DNAzyme functionalized NANs after 4 h at 37° C.: lane 1, truncated mRNA free in solution; lane 2, post incubation with DNAzyme-NANs; lane 3, mutated DNAzyme-NANs without salts; lane 4, mutated DNAzyme-NANs with salts; and lane 5, DNAzyme off particle, showing complete cleavage of the truncated mRNA target. Mutated DNAzyme details in Table 1. Panel B shows the DNAzyme-NAN is able to cleave a fluorescently labeled mRNA truncate that is quenched prior to cleavage but becomes fluorescent post cleavage. In the presence of the DNAzyme-functionalized NANs, the mRNA truncate (10 nM) is rapidly cleaved as shown above. DNAzyme concentrations used in the ligation reaction can result in multiple DNAzymes per NAN. Fluorescence traces are shown to indicate activity versus lack of activity. Free DNAzyme (500 nM) along with NANs functionalized with mutated DNAzyme-NANs (both at 100 nM) are shown as positive and negative controls for activity, respectively. (C-F) Cells treated with 1 μM rhodamine B loaded NANs: (C) green emission channel indicating the location of the rhodamine B NANs in cells; (D) Lysotracker Red staining of lysosomes and endosomes within cells; (E) co-localization of NANs and lysosomes showing the NANs enter the cells through endocytosis; (F) brightfield image and overlay. Scale bar is 25 μm.

The DNAzyme-functionalized NANs were first incubated with an mRNA truncate of GATA-3 and then evaluated for evidence of mRNA cleavage in vitro. The DNAzyme-functionalized NANs were shown to be effective at cleaving a truncated GATA-3 mRNA sequence at 37° C. after 4 h as indicated by polyacrylamide gel electrophoresis (FIG. 5A). To probe the relative amount of cleavage of the mRNA truncate in the presence of the DNAzyme-functionalized NAN, a modified mRNA truncate containing a dye (FAM) and a dye quencher (BHQ-1) was monitored using fluorescence spectroscopy. In the presence of 100 nM DNAzyme-NANs, 10 nM mRNA truncate is fully cleaved within the first hour of incubation as indicated by the increase in fluorescence observed (FIG. 5B). These results indicate that the particle surface can be easily modified using enzymes with functional, therapeutic nucleic acids.

Example 3: Preparation and Evaluation of Peptide-Crosslinked NANs

Figure 6:
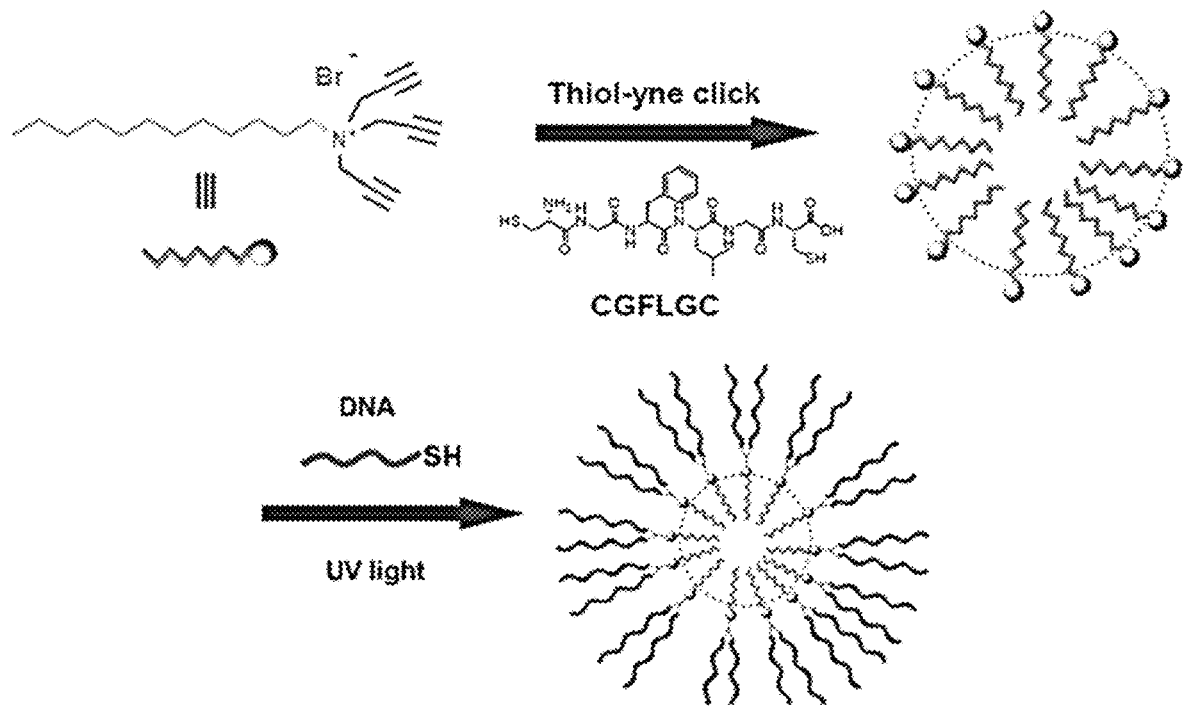
FIG. 6 shows a stepwise assembly of peptide-crosslinked Nucleic Acid Nanocapsules (pep-NANs).

Peptide Surface Crosslinked Micelles (pep-SCMs): A typical procedure is illustrated in FIG. 6. For example, 1.9 mg of surfactant 1 was dissolved in Millipore water (500 µL). 31.25 µL of a 4 mM 5-carboxytetramethylrhodamine (5-TAMRA) stock solution in DMSO was added to the micelle solution and allowed to stir for 30 minutes at room temperature. 17 µL of either CGFLGC (cathepsin B substrate) (SEQ ID NO:8) or CGPLGLAGGERDGC (MMP9 substrate) (SEQ ID NO:9) was added to 232 µL of the micelle solution. 1 µL of 2-hydroxy-4-(2-hydroxyethoxy)-2-methylpropiophenone (DHEMPP) was also added, resulting in the following final concentrations: surfactant (9.28 mM), 5-TAMRA (250 µL), peptide crosslinker (5 mM) and DHEMPP (20 µM). The final solution was placed in a Rhyonet reactor for 30 minutes. The product was characterized by DLS and zeta potential on a Zetasizer Nano-ZS90, by TEM, and by 1% agarose gel electrophoresis.

Peptide Nucleic Acid Nanocapsules (pep-NANs): 5 µL of pep-SCMs was diluted to a total volume of 500 µL to give a concentration of 92.8 µM. Included in this dilution was 38.5 µL of a thiolated DNA (100 µM) and 1 µL of 2-hydroxy-4-(2-hydroxyethoxy)-2-methylpropiophenone (20 µM). The final solution was placed in a Rhyonet reactor for 30 minutes. The product was purified by Sephadex G-25 NAP-10 column. The product was characterized by DLS and zeta potential on a Zetasizer Nano-ZS90, TEM, and by 1% agarose gel electrophoresis.

Figure 7:
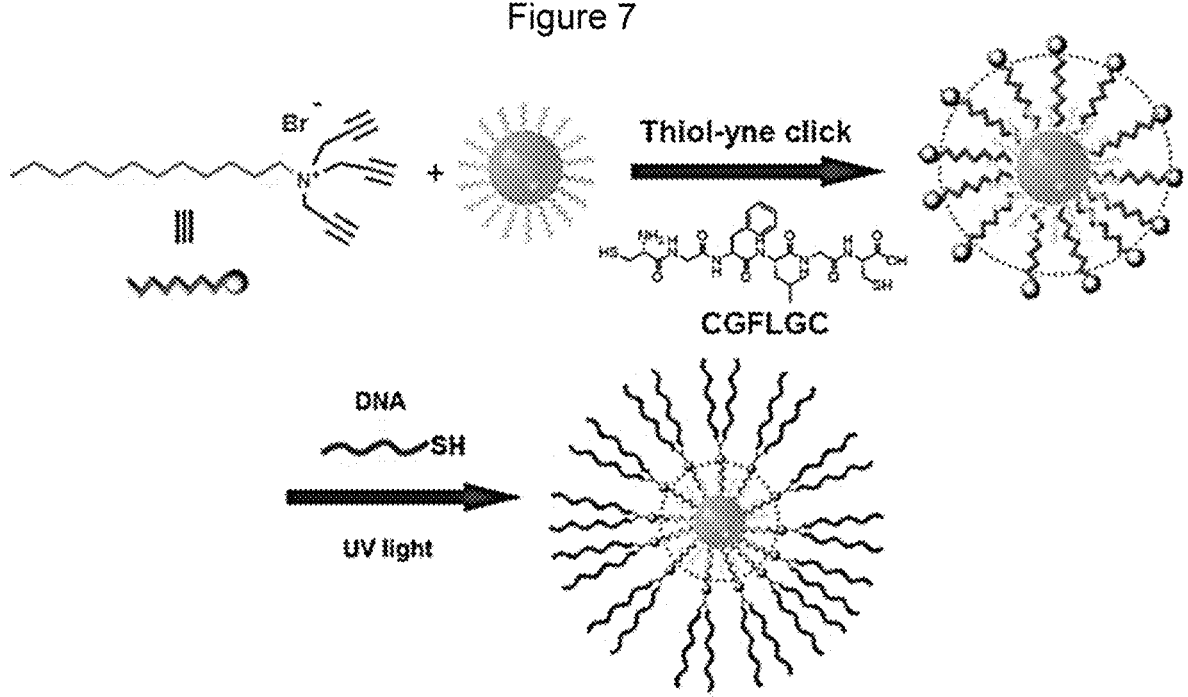
FIG. 7 shows a stepwise assembly of gold nanoparticle encapsulated peptide-crosslinked Nucleic Acid Nanocapsules (pep-Au-NANs).

Example 4: Preparation and Evaluation of Gold Nanoparticle Encapsulated Peptide-Crosslinked NANs Gold Nanoparticle Encapsulated Peptide Surface Crosslinked Micelles (pep-Au-SCMs): A typical procedure is illustrated in FIG. 7. For example, 10 µL of tetradecylamine functionalized gold nanoparticles in cyclohexanes were air dried. 1.5 mg of surfactant was added to 500 µL of water and 20 µL of hexanes giving a final concentration of 7.62 mM by surfactant. This solution was allowed to stir overnight. The solution was diluted to 1 mL giving a new concentration of 3.81 mM by surfactant. 12 µL of either CGFLGC (cathepsin B substrate) (SEQ ID NO:8) or CGPLGLAGGERDGC (MMP9 substrate) (SEQ ID NO:9) was added to 487 µL of the AuNP micelle solution. 1 µL of DHEMPP was also added, giving these final concentrations: surfactant (3.71 mM), peptide crosslinker (2 mM) and DHEMPP (20 µM). The final solution was placed in a Rhyonet reactor for 30 minutes. The product was centrifuged for 15 minutes at 8,000 rpm and the supernatant was removed. This was repeated 3 times and the pep-Au-SCMs were reconstituted in 250 µL of Millipore water. The product was characterized using DLS, zeta potential measurements, and TEM.

Gold Nanoparticle Encapsulated Peptide Nucleic Acid Nanocapsules (pep-Au-NANs): 6 µL of pep-Au-SCMs was diluted to a total volume of 500 µL to give a concentration of 100 uM. Included in this dilution was 38.5 µL of thiolated DNA (100 µM) and 1 µL of 2-hydroxy-4-(2-hydroxyethoxy)-2-methylpropiophenone (20 µM). The final solution was placed in a Rhyonet reactor for 30 minutes. The product was centrifuged for 15 minutes at 8,000 rpm and the supernatant was removed. This was repeated 3 times and the pep-Au-NANs were reconstituted in 250 μL of Millipore water. The product was characterized using dynamic light scattering, zeta potential, and transmission electron microscopy.

Gold Nanoparticle Encapsulated Nucleic Acid Nanocapsules (Diol/Ester-Au-NANs): A modified protocol from above was used to synthesize gold encapsulated diol and ester NANs. Gold encapsulated diol NANs was prepared by reacting surfactant 1 with 1,4-diazidobutane-2,3-diol (3). Gold encapsulated ester NANs was prepared by reacting surfactant 1 with diazide crosslinker 2.

Discussion:

Many sensing applications attempt to determine the presence of enzymes expressed, which can vary dramatically during the course of a cell's life, and differ depending on different disease states. With this in mind, well-studied cathepsin B and MMP9 were tested. In addition to their implication in several cancer types, importantly, MMP9 is located in the extracellular matrix (ECM) of cells, and functions optimally at physiological pH (pH 7), whereas cathepsin B is an endosomal protease that functions optimally at pH 5. As a control the localization of these enzyme-responsive peptide cross-linked-nucleic acid nanocapsules (pep-NANs) was compared to the activity of ester-crosslinked and non-ester, diol crosslinked NANs of Example 1 using electron microscopy.

Figure 8:
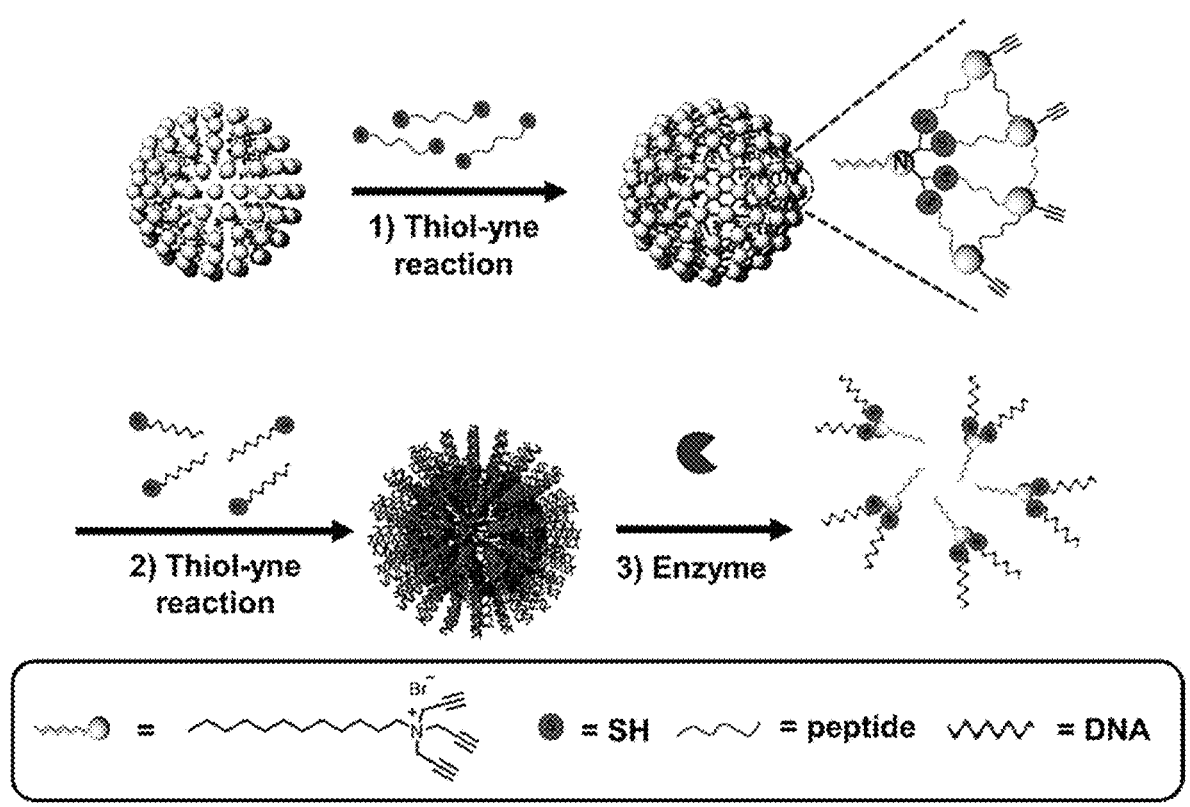
FIG. 8 illustrates assembly and programmed degradation of peptide crosslinked nucleic acid nanocapsules (pep-NANs). Peptide sequences of interest are modified with terminal cysteines to provide thiolated attachment points for covalently photo-cross-linking peptides to the alkyne-modified nanocapsule surface. The cross-linkers are incorporated using thiol-yne chemistry in the presence of a photoinitiator and UV light.
Figure 9:
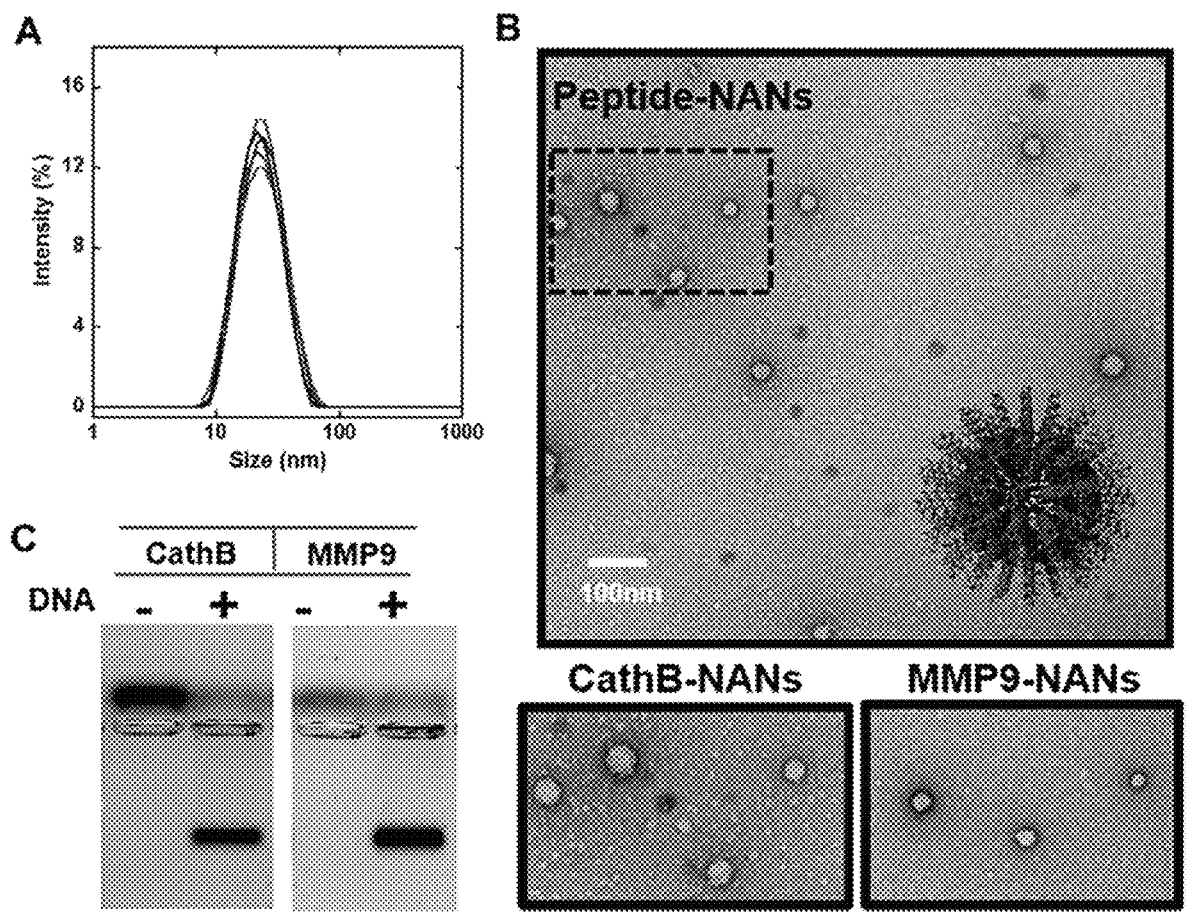
FIG. 9 shows nanoscale characterization of peptide cross-linked NANs. (A) Representative DLS measurement of peptide-cross-linked NANs (DLS and zeta potential values are in Table 2). (B) Representative transmission electron micrographs showing peptide cross-linked NANs stained with 0.5% uranyl acetate for both CathB and MMP9 peptide substrates. Dotted outline indicates region of micrograph expanded for CathB NANs. (C) 1% agarose gel showing the change in mobility of individual pep-NANs (CathB-NAN and MMP9-NAN) post attachment of a thiolated polyT20 DNA ligand using UV light-driven thiol-yne chemistry.

By introducing a peptide substrate whose sequence was modified at both the N and C terminus with cysteine residues to allow for chemical attachment points (thiols) for reacting with the alkynes presented at the surface of the NAN's micellular core (FIG. 8). Characterization of the successful assembly of the pep-NANs was achieved using a combination of dynamic light scattering (DLS), transmission electron microscopy (TEM), zeta potential measurements, and gel electrophoresis (FIG. 9). Collectively these results indicated nanocapsule populations approximately 35 and 24 nm in size for cathepsin B peptide substrate linked NANs (CathB-NANs) and matrix metalloproteinase 9 peptide substrate linked NANs (MMP9-NANs), respectively (FIG. 9B, Table 2).

Figure 10:
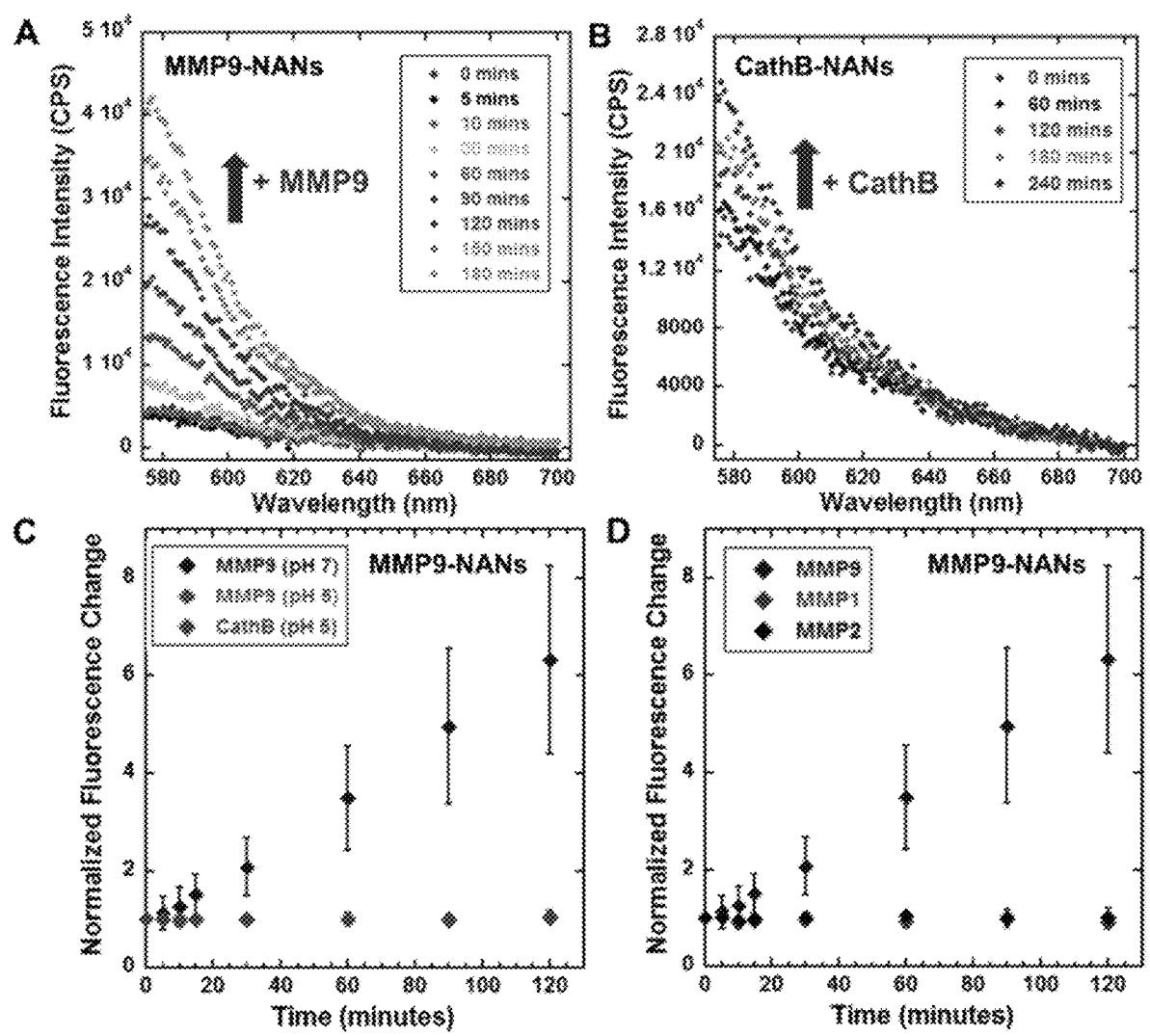
FIG. 10 illustrates fluorescence monitoring of pep-NAN degradation. (A) Representative raw fluorescence intensity plots showing the release of dye from MMP9-NANs cross-linked with MMP9 peptide in the presence of MMP9 enzyme. One μM MMP9-NANs were treated with 0.5 μg of MMP9 and monitored for 3 h. (B) Dye-loaded CathB-NANs in the presence of 0.5 μg of cathepsin B monitored for 3 h. (C) Fluorescence monitoring of cathepsin B activity on MMP9-NANs and the effect of varying pH on MMP9 cleavage rates. Exposure of MMP9-NANs to cathepsin B and MMP9 at pH 5 resulted in no observable change in fluorescence. (D) Fluorescence plots of MMP9-NANs treated with MMP1 and MMP2 lacked the specificity to cleave the MMP9-NANs at pH 7. All experiments were conducted in triplicate.

A fluorescence assay was used to monitor the rate and extent of dye release (FIG. 10) in order to test individual enzyme specificity for the peptide substrates within each pep-NAN. MMP9-NANs and CathB-NANs released their dye when treated with their intended enzyme targets, MMP9 and cathepsin B, respectively (FIG. 10 A,B). Cathepsin B activity on MMP9-NANs was also evaluated, in which no fluorescence change was observed (FIG. 10C). This indicates that proteases from different families of enzymes are less likely to recognize the substrates of other enzymes within the pep-NAN formulations. The results of these experiments also indicated that the pH of the solution can control the release or lack of release of dyes from a pep-NAN formulation despite the presence of the appropriate enzyme trigger in solution. To test the relative rate of cleavage of the MMP9-NANs in the presence of closely related MMP enzymes, the MMP9-NANs was treated with various MMP proteins, including MMP1 and MMP2 (a collagenase and a gelatinase, respectively), both of which function optimally at pH 7. The results of these experiments indicated that the MMP9-NAN is specific to the MMP9 enzyme (FIG. 10D). Additional MMP enzymes were also tested, showing a similar inability to cleave the MMP9-NANs (results not shown).

Dye-loaded pep-NANs were also incubated with HeLa cells and observed under confocal microscopy (results not shown). Both the CathB and MMP9 NANs entered cells readily when incubated in serum free conditions (FIG. 11A) indicating that, like other spherical nucleic acid structures, they do not require addition of external transfection agents. The pep-NANs were also examined in cells over a range of concentrations in order to assess their relative toxicity in cell culture. The resulting cell survival indicated little to no toxicity for both the CathB-NANs and the MMP9-NANs indicating their potential use in both in vitro and cell culture settings.

Figure 11:
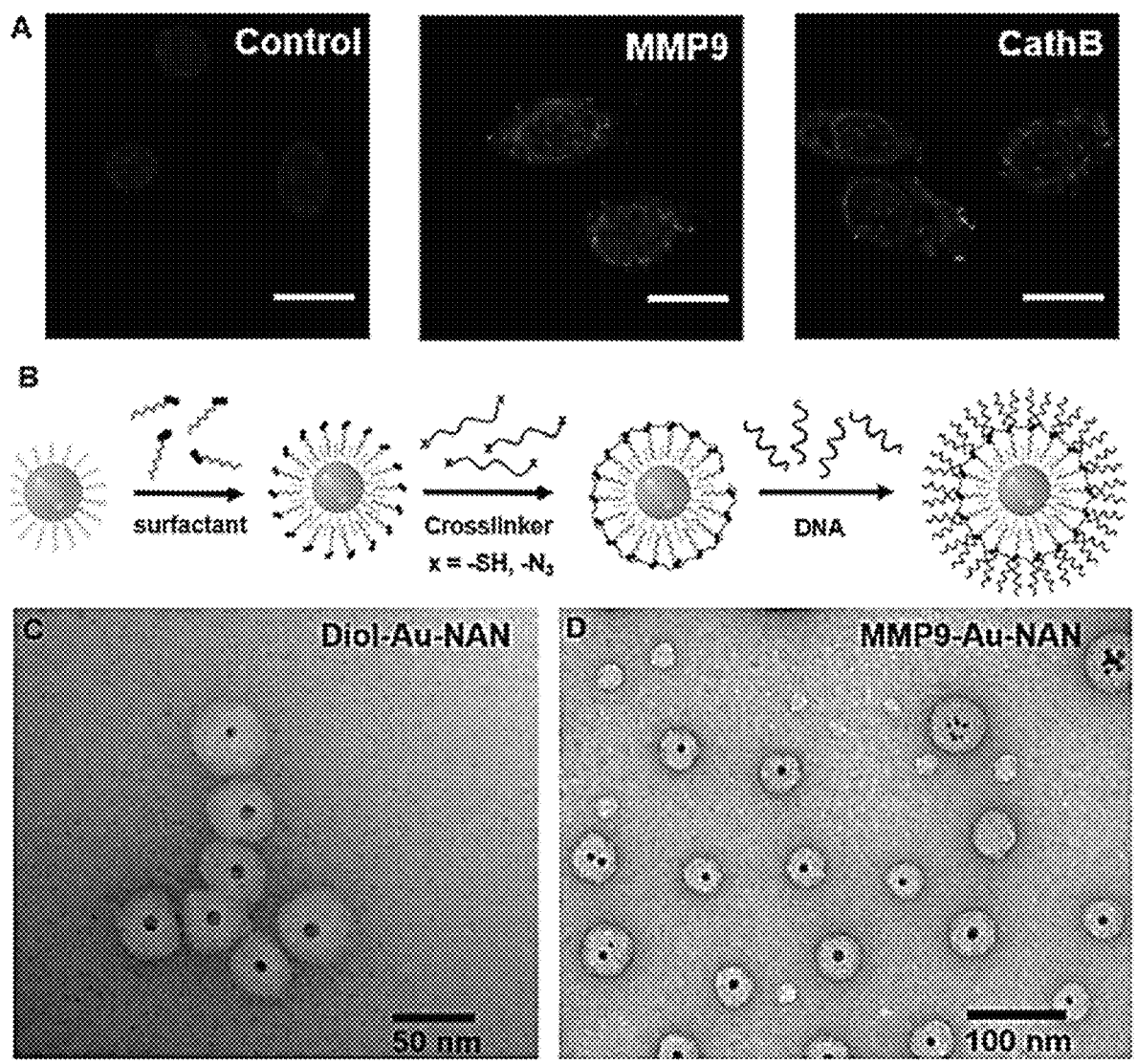
FIG. 11 shows confocal and electron microscopy of pep-NANs. (A) Confocal microscopy of pep-NANs (MMP9 and CathB) indicating cellular uptake. (B) Schematic depicting the assembly of a pep-Au-NAN where the cross-linker consists of either esters, diols, or peptides, cross-linked using either Cu(I) azide alkyne catalyzed click chemistry or thiol-yne chemistry, depending on the terminal modification presented by the cross-linker. (C) TEM of diazido-diol (compound 3) cross-linked NANs, individual shells could be seen surrounding the Au NP by TEM when stained with 0.5% uranyl acetate. (D) TEM of MMP9-NANs formed in the presence of an alkane-modified AuNP. Similar to the diol-cross-linked NANs, individual particles can be seen containing AuNPs incorporated into their centers.

To be able to engage individual populations of enzymes in specific cellular locations for regulating cargo release, it became particularly important to develop a more precise way of tracking the pep-NANs intracellularly in order to be able to anticipate the biochemical environment that they would experience. To visualize the nanocapsules intracellularly, a protocol for encapsulating gold nanoparticles (AuNPs) into the interior of the pep-NANs was developed. Starting with a 10 nm tetradecylamine-modified AuNP, the addition of surfactant in water was used to build the NAN's exterior shell around the alkane-functionalized AuNP (FIG. 11B). The gold nanoparticle-embedded NANs, referred to here as pep-Au-NANs, were incubated with HeLa cells to reveal the intracellular location post uptake and to determine if the stability of the pep-NANs could be visualized (i.e., shell intact or degraded) using uranyl acetate staining of charged organic species. Using this approach, both pep-NANs and chemically crosslinked NANs could be successfully visualized (FIG. 11C,D). By controlling the stoichiometric ratio of surfactant, AuNP and cross-linker, roughly 1 AuNP per NAN could be achieved per particle, regardless of cross-linker utilized, as observed by TEM (data not shown).

Figure 12:
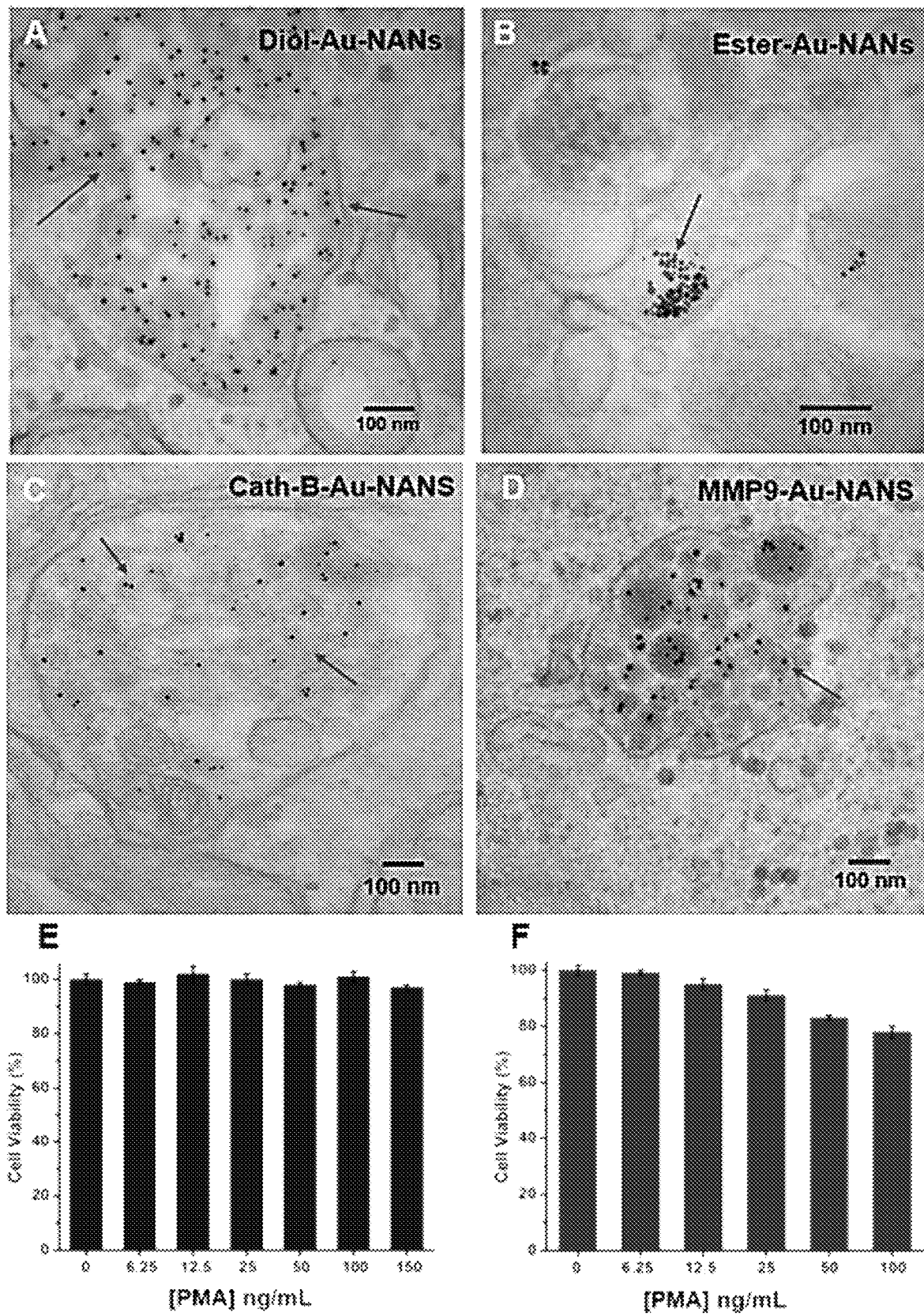
FIG. 12 shows cellular uptake of AuNP embedded NANs visualized through cell sectioning and staining using TEM. (A) TEM of a diazido-diol cross-linked NAN inside a sectioned HeLa cell. (B) Ester-Au-NANs, used as a positive control, observed within endosomes by TEM. In TEM micrograph of (C) CathB-Au-NANs and (D) MMP9-Au-NANs intact peptide shells can be observed within the cells. (E) HeLa cells treated with PMA (MMP9 inducer) for 21 h show no toxicity up to 150 ng/mL. (F) HeLa cells treated with PMA for 21 h followed by incubation with 40 μM MMP9-NANs loaded with 2.5% camptothecin. The results indicate that only after PMA induction of MMP9 is toxicity of the drug loaded pep-NANs observed.

After characterizing the pep-Au-NANs, they were incubated with HeLa cells and subsequently sectioned, stained, and imaged for evidence of pep-Au-NAN uptake into cells (FIG. 12A-D). As shown in FIG. 12, diverse formulations of the Au-NANs could be found within endosomes with varying degrees of stability, within the cross-sectioned HeLa cells. In FIG. 12A,B the negative and positive controls for NAN disassembly are shown (negative control is a diazido-diol cross-linker, compound 3, and the positive control is the ester cross-linker, compound 2). As anticipated, the diazido-diol cross-linked NANs could not release their cargo in the endosomes, and the ester-cross-linked NANs could, giving us an image of what an intact and degraded NAN shell looks like intracellularly, respectively. This interpretation is based

TABLE 2

Average pep-NAN DLS and zeta potential data.

| Measurement | CathB-SCM | CathB-NAN | CathB-Au-NAN | MMP9-SCM | MMP9-NAN | MMP9-Au-NAN |
|---|---|---|---|---|---|---|
| DLS | 30.2 ± 2.7 | 34.8 ± 5.2 | 30.2 ± 4.8 | 27.3 ± 2.4 | 23.6 ± 2.0 | 33.1 ± 1.8 |
| Zeta Potential | 47.0 ± 2.5 | −30.8 ± 6.6 | −41.9 ± 2.8 | 41.6 ± 2.6 | −37.9 ± 6.7 | −45.4 ± 2.1 |

SCM = surface crosslinked micelle, NAN = nucleic acid nanocapsule.

on the fact that an intact gray halo, similar to those seen in FIG. 11C,D, is clearly seen surrounding each of the AuNPs in the endosomal compartments in FIG. 12A. In addition, the lack of organic stained halo seen in FIG. 12B along with the aggregated nature of the AuNPs suggests the loss of surface functionalization.

The results of these studies indicate that the NAN's outer structure could indeed dictate the release of the cargo from the nanocapsule. This was seen in the context of both the chemically cross-linked as well as peptide-cross-linked NANs. Importantly, the MMP9-NANs did not open despite being endocytosed, which correlates well with the fact that MMP9 enzyme is not expressed intracellularly, nor secreted in significant levels by HeLa cells. Cathepsin B, although found in HeLa cells, did not open the CathB-NANs, potentially due to the incubation time within the HeLa cells might not have been long enough to result in the breakdown of the pep-NANs.

The later reasoning is thought to be the case based on the degradation rate observed in vitro in the fluorescence assay results (results not shown). The results show it takes ~20× as long to see comparable fluorescence changes in solution when cathepsin B is added to a solution of CathB-NANs as compared to MMP9-NAN degradation by MMP9. Additionally, it is important to consider that enzyme concentrations rise and fall depending on the current level of mRNA expression, and can be dysregulated (often overexpressed) when cells become diseased.

In order to test the correlation between enzyme expression level within a live cell and the ability of the pep-NANs to be degraded, an additional assay was run in which HeLa cells were treated with phorbol 12-myristate 13-acetate (PMA), a known inducer of MMP9 expression in HeLa cells. Cells were incubated in serum-free media and treated with MMP9-NANs carrying camptothecin, a known apoptotic cancer drug. The toxicity of the drug loaded MMP9-NANs was evaluated using an MTS assay post 21 h PMA treatment, allowing enough time for MMP9 expression. These studies resulted in a dose dependent increase in cellular toxicity, interpreted as a response to the PMA inducing MMP9 expression and secretion by the HeLa cells, ultimately catalyzing the release of the drug in response to the pep-NAN's enzyme target (FIG. 12E,F). Treatment of PMA and drug loaded MMP9-NANs without allowing time for MMP9 secretion resulted in no cell toxicity.

In conclusion, the peptide-NANs were found to have important advantages in controlling the release of cargo in cell specific locations. This added level of control and specificity over degradation and release of internalized cargo, coupled with the rapid and modular nature of the assembly approach, offers significant advantages of the multifunctional nanoparticles of the disclosure. In one embodiment, for example, the hybrid peptide-based multifunctional nanoparticles of the disclosure are suitable for various therapeutic and diagnostic applications.

Example 5: Preparation and Evaluation of DNAzyme Ester-Crosslinked NANs (DNAzyme-NAN)

GATA-3 targeting DNAzyme (hgd40) (Sel et al. *J. Allergy Clin. Immunol.* 2008, 121, 910-916; Krug et al. *N. Engl. J. Med.* 2015, 372, 1987-1995.) was chosen as the proof of concept sequence for evaluating the gene regulation capabilities of the DNA surfactants in cell culture for its well-studied activity in vitro and in vivo using traditional delivery methodologies. The GATA-3 gene is of particular biological importance as it regulates downstream inflammation responses in immune cells. It has been a target gene of interest for diseases such as asthma and chronic inflammatory diseases.

Nucleic Acid Nanocapsule (NAN) Synthesis: 1.9 mg of surfactant 1 (0.005 mmol) was dissolved in 483.2 µL Millipore water. Solution was stirred at room temperature for 30 minutes. 10 µL of a 25 mg/mL sodium ascorbate solution (0.00125 mmol), 5 µL of a 25 mM THPTA-Cu complex (0.000125 mmol), and 1.8 µL esterified diazido cross-linker 2 (0.006 mmol) were added to a total volume of 500 µL. Mixture was stirred at room temperature for 3.5 hours. The product was purified by a Sephadex G-25 NAP-10 column (GE Healthcare), and the fractions containing surface cross-linked micelles (SCMs) were characterized through dynamic light scattering (DLS) and zeta potential. A solution containing 100 µM SCMs, 150 µM thiolated DNA, and 20 µM of 2-hydroxy-4-(2-hydroxyethoxy)-2-methylpropiophenone (DHEMPP) in a total volume of 500 µL was placed in a Rhyonet reactor for 30 minutes. The resulting product was purified by a Sephadex G-25 NAP-10 column, and the fractions were characterized by DLS and zeta potential measurements on a Malvern Zetasizer Nano Z590.

Ligation of DNAzyme to Nucleic Acid Nanocapsule (NAN): 20 µM GATA-3 DNAzyme (SEQ ID NO:2) and 40 µM DNAzyme bridge (SEQ ID NO:3) were added to 10 µM NANs functionalized with DNA anchor (SEQ ID NO:1). Water was added to a total volume of 300 µL. The solution was heated at 70 µC for 10 minutes and cooled to room temperature. 5 mM ATP, 15 µL of 1 U/µL T4 DNA Ligase (Invitrogen), and 1× ligase buffer were mixed. Water was added to a total volume of 300 µL. Placed on a 25° C. heat block for 2 hours. Ligase was heat inactivated at 65° C. for 10 minutes. Product was washed through a Sephadex G-25 NAP-10 column. Fractions were then analyzed by DLS to purify unligated DNAzyme from DNz-NANs.

DNAzyme Stability Assay: To determine the stability of the DNAzyme ligands on the NANs, 1.5 µM free DNAzyme and 1 µM DNz-NANs were incubated in either phosphate buffered saline (PBS, VWR International) or 10% fetal bovine serum (FBS, ThermoFisher Scientific) for 1 hour at 37° C. After incubation, products were amplified through 35 cycles of PCR and run on an 8% denaturing polyacrylamide gel.

Quantification of DNAzymes/NAN: Equivalent volumes of 8 M urea and TYE563-DNAzyme functionalized NANs were heated at 70° C. for 10 minutes and purified by a Sephadex G-25 NAP-10 column. Fluorometric measurements were taken of fraction 3 with a Horiba Jobin Yvon Fluorolog 3 series fluorometer. Excitation: 549 nm. Scan: 563-625 nm. TYE563-DNAzyme values were compared to a standard curve to obtain the final DNAzyme concentration. Typical starting concentrations of DNAzyme-NANs were 125 nM or 250 nM.

Kinetics Cleavage Assay: To determine the kinetics of the cleavage of GATA-3 by both the free and NAN-bound DNAzyme, a fluorescence-based assay was developed. A mRNA truncate corresponding to the cleavable sequence in GATA-3 mRNA was purchased (BioSearch Technologies). The truncate, herein referred to as BHQ-mRNA, was functionalized with a quencher (BHQ1) at the 3' end and a fluorescein derivative (FAM) at the 5' end. BHQ-mRNA was shown to be stable at relevant salt concentrations [MgCl2 (10 mM), NaCl (100 nM)] and at the relevant temperature (37° C.) and was therefore deemed suitable for the kinetics study. All fluorescence measurements were taken using a Horiba Jobin Yvon fluorometer and, unless otherwise stated, all samples were excited at 470 nm and measurements taken from 485 nm to 4700 nm. Samples were heated to their stated temperature using a Cary single cell peltier accessory. A solution of MgCl2 (10 mM), NaCl (100 mM), DNAzyme (10 nM) and H$_2$O was prepared in a total volume 400 μL. The DNAzyme solution was heated to 70° C. for ten minutes prior to mixing. The sample was cooled to and held at 37° C. in the fluorometer and an initial background reading was taken. BHQ mRNA (10 nM, BioSearch Technologies) was spiked into the sample and the fluorescence monitored over 20 minutes. Additional measurements were taken at 25, 50, 75, and 200 nM concentrations of mRNA. This same procedure was repeated for the DNAzyme-NAN (10 nM). Note, as it was determined that there are approximately 2 DNAzymes per surfactant molecule in a given DNz-NAN assembly, the value of 20 nM DNAzyme was utilized for the ([ET]) in the Kcat calculation. Kcat=Vmax/[ET]. For the free DNAzyme calculation, 10 nM was used for ([ET]). All non-linear fits for assigning Vmax values were determined using Kaleidagraph 4.5 graphing software.

Figure 13:
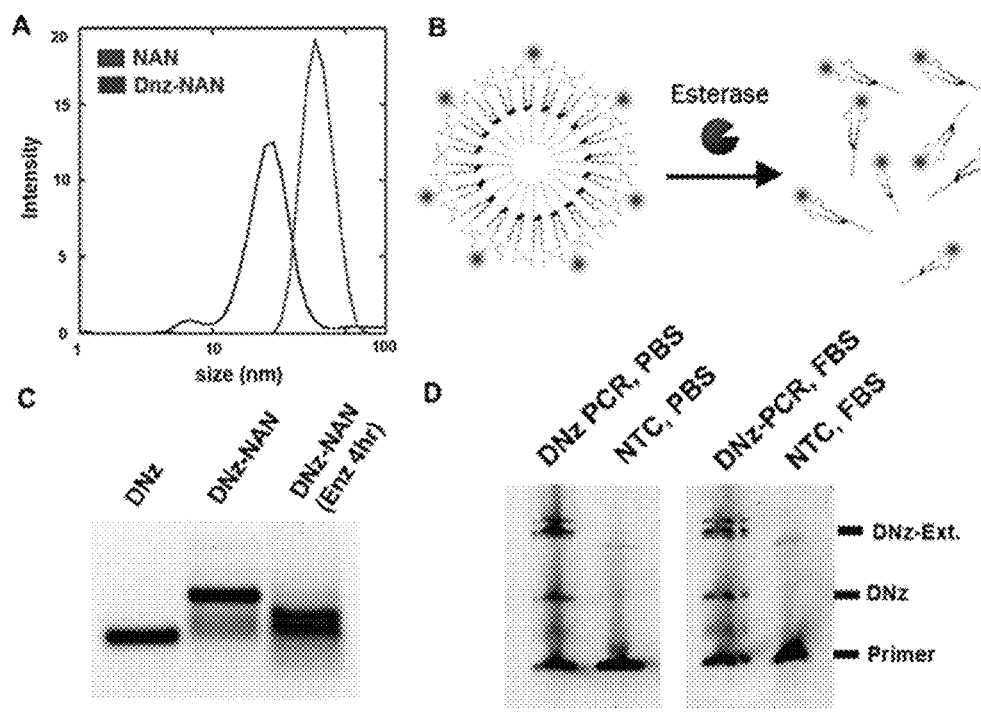
FIG. 13 illustrates characterization and stability studies of the DNAzyme NAN structure of Example 5. (A) Dynamic light scattering data pre- and post-DNAzyme ligation to the nanocapsule. (B) Schematic depicting the cleavage of the ester-linked, dye-labeled nanocapsule, resulting in the release of fluorescent DNAzymes bound to surfactant molecules. (C) 3% agarose gel showing the shift in free DNAzyme vs. DNz-NAN vs. the enzymatic cleavage products after 4 hours of esterase treatment. (D) PCR amplification of full length DNAzyme after incubation of free DNAzyme and DNAzyme-NANs in PBS or 10% FBS in PBS. Dnz-Ext represents the extension of the DNAzyme on the 5' end due to the primer annealed to the DNA anchor at the particles surface, indicating full length DNAzyme remains intact post exposure to serum nucleases.

Discussion:

Ester-crosslinked NANs were treated with T4 DNA ligase to provide DNAzyme covalently assembled at the nanocapsules. The DNAzyme was synthesized using automated DNA synthesis and ligated to a DNA anchor at the NANs surface. Characterization of all DNAzyme-NAN materials used in these studies consisted of dynamic light scattering (DLS) (FIG. 13A) and agarose gel electrophoresis shift assays (FIG. 13C). The average size of the micellular core was shown to increase from 23.4±5 nm to 63.5±10 nm post DNA attachment, indicative of addition of the DNAzyme to the surface of the DNA-functionalized nanocapsule. This can be determined based on the fully extended length calculation for the unfolded DNAzyme, a 33mer sequence.

Figure 14:
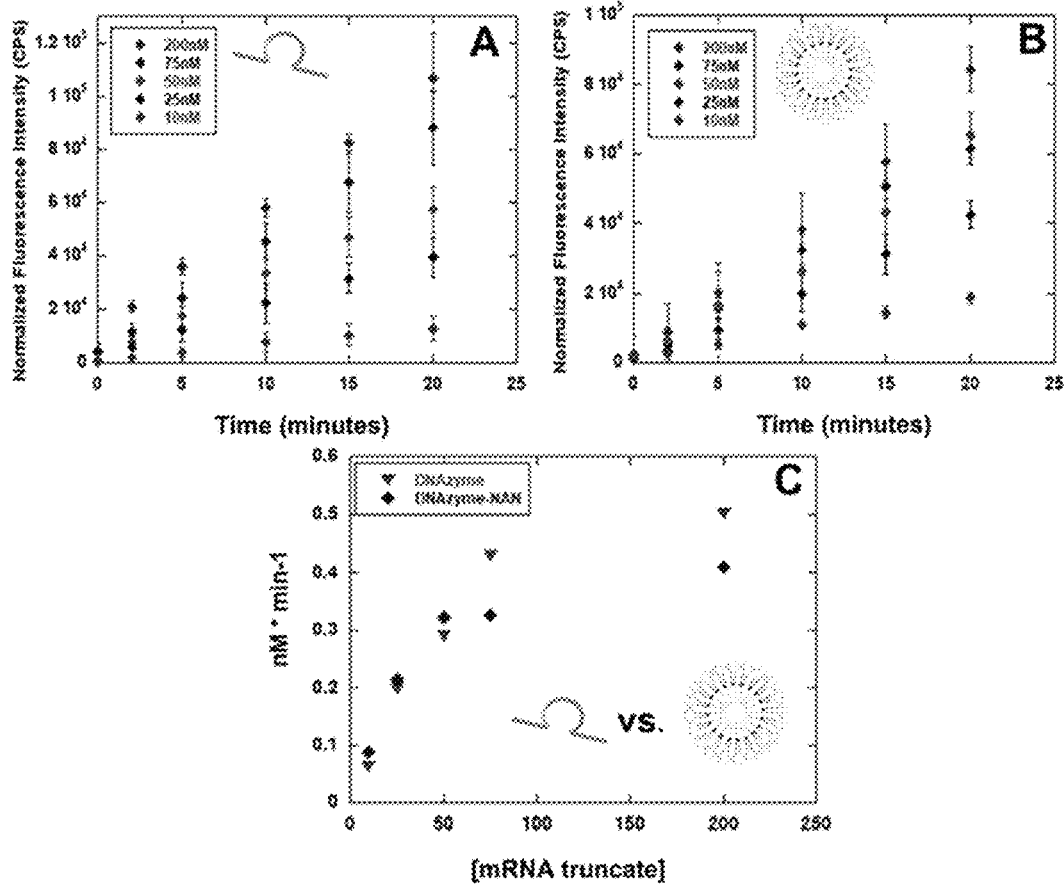
FIG. 14 illustrates fluorometric kinetic analysis of mRNA cleavage rates for a free DNAzyme versus a DNAzyme-NAN. (A) Initial rates of cleavage for the free DNAzyme with various concentrations of mRNA substrate (B) Initial rates of cleavage for the immobilized DNAzymes ligated to DNA-surfactants on the NANs. For both (A) and (B), each data point is the average of triplicate runs, with standard deviations reported. (C) Maximal rates of cleavage are plotted as a function of mRNA substrate concentration. The free DNAzyme (triangles) trace is plotted versus immobilized DNAzymes tethered to DNA-surfactant molecules (diamonds). The plots indicate similar rates of cleavage but that the overall catalytic activity of the DNAzyme is slightly more efficient than the immobilized DNz-NAN, interpreted as due to steric effects at the nanocapsules surface due to DNAzyme crowding.

To determine the total number of DNAzymes per surfactant, the DNAzyme was modified with a 5' terminal TYE-563 dye, and ligated to the NANs. Unligated dye labeled DNAzymes were then removed by size exclusion chromatography. Using a standard curve of the emission from the TYE-563 dye labeled DNAzyme, the remaining fluorescence of the NANs post DNAzyme ligation could be determined and used for subsequent concentration calculations for treatment with cells. Notably, the average number of DNAzymes per surfactant came out to be 2.3±0.2. This suggests a highly efficient stepwise construction of DNA ligands on the surface of the nanocapsule. Attachment of the oligonucleotides occurs in two steps, starting with the photocatalyzed attachment of the 5' thiolated DNA anchor to the terminal alkynes of the crosslinked micelle's surfactant molecules, followed by enzymatic ligation of the DNAzymes to the DNA anchor molecules. Once assembled, comparative DNAzyme cleavage kinetics were investigated using a fluorophore and quencher labeled GATA-3 mRNA truncate (19mer) described previously. Upon cleavage of the labeled mRNA target, a quenched dye becomes fluorescent and can be monitored as a function of substrate concentration over time. DNAzyme concentration was held constant (10 nM) and the concentration of mRNA truncate varied from 10-200 nM. The rate of cleavage was monitored over the course of 20 minutes. Changes in fluorescence were plotted and the initial rise at each concentration was fit to determine an observed rate of cleavage per nanomolar amount of substrate (FIG. 14). The results indicate that the DNAzyme follows a classical Michaelis-Menten type model of saturation kinetics, with the rate of cleavage saturating at higher mRNA substrate levels (FIG. 14). The relative rates of cleavage by the DNAzyme versus the DNz-NAN are shown to be roughly comparable. The DNAzyme was determined to have a $K_m$ of 59 nM and a $K_{cat}/K_m$ of $1.1\times10^6$ M$^{-1}$ min$^{-1}$, whereas the DNz-NAN had a $K_m$ of 32 nM, and a $K_{cat}/K_m$ of $7.5\times10^5$ M$^{-1}$min$^{-1}$. This indicates that the immobilization of the DNAzyme on the NANs surface by its 5' end enables a rapid rate of cleavage but a slightly decreased activity overall, likely due to the crowded surface on the nanocapsule as a result of neighboring DNAzymes. However, the constructs differ in efficiency by a factor of roughly 1.5, indicating that when tethered, the DNAzyme does not suffer a significant decrease in activity as has been observed in other colloidal DNAzyme systems.

Figure 15:
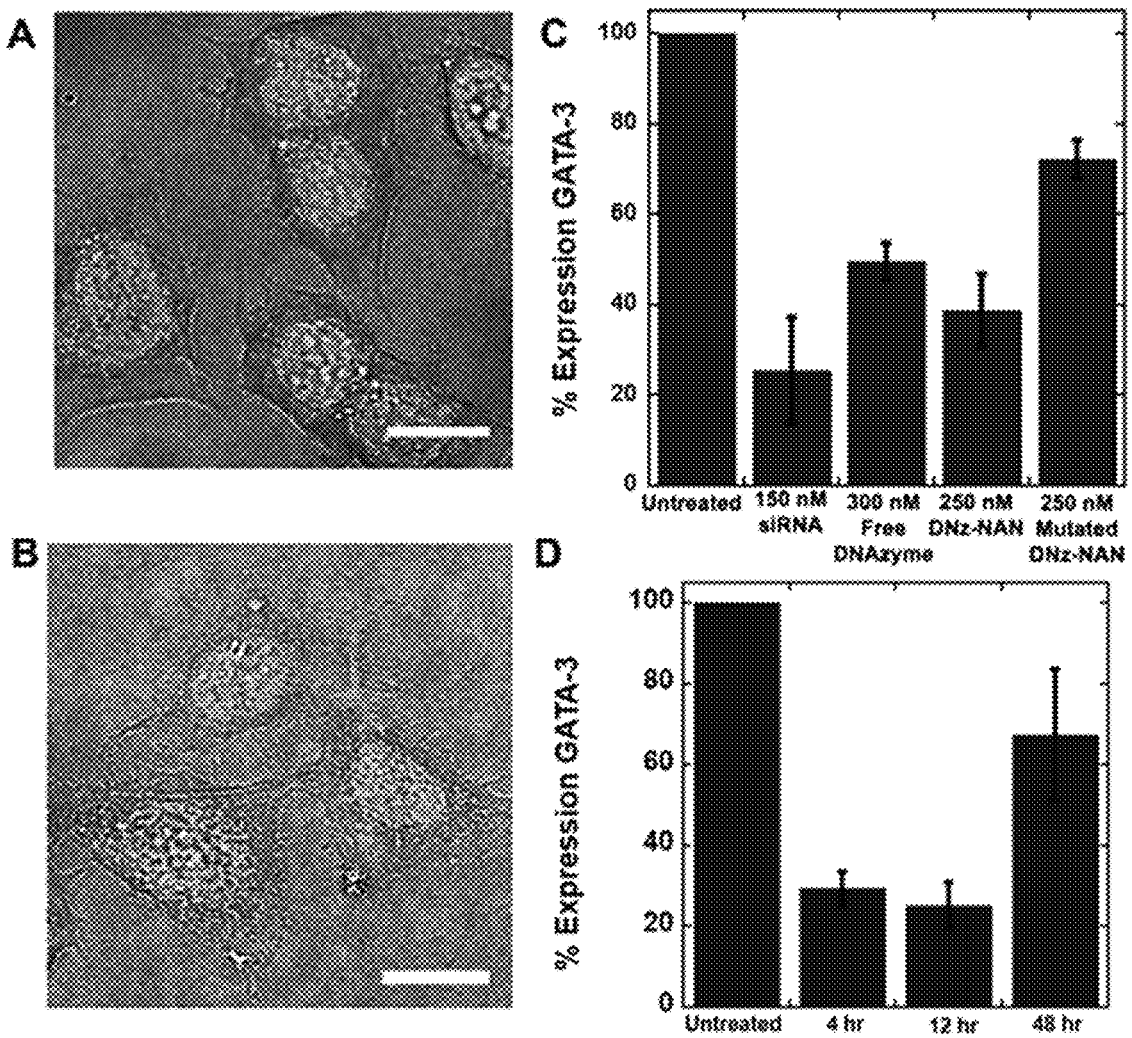
FIG. 15 illustrates cellular uptake and targeted gene knockdown by DNAzyme-NANs in MCF-7 cells. (A) Confocal microscopy of free DNAzymes labeled with TYE-665 dye transfected into MCF-7 cells and monitored for evidence of cellular uptake post 4 hours of incubation. (B) Confocal microscopy of DNz-NANs incubated with cells without transfection agents in which the DNAzyme on the NAN was also labeled with TYE-665 dye. In both cases, TYE signal could be observed in the perinuclear region of the cells. All scale bars are 20 μm. (C) GATA-3 mRNA knockdown in MCF-7 cells. 250 nM DNz-NAN is capable of knocking down mRNA by 60% compared to untreated cells (N=3, p=0.0016). There is no significant difference in mRNA knockdown with 150 nM siRNA and 250 nM NAN (N=3, p=0.406). Error bars represent the standard error of the mean (N=3). (D) MCF-7 cells treated with 250 nM DNz-NANs, monitored for GATA-3 mRNA levels via qRT-PCR at times ranging from 4 to 48 hours of incubation.

Targeted cleavage is only possible if the DNz-NAN can disassemble and the DNz-surfactants can escape the endosomal compartments of the cell post endocytosis. To study the suitability of the DNz-NAN for cellular uptake and stability of its DNAzyme ligands in the cell, the DNz-NANs were first incubated in 10% fetal bovine serum to mimic exposure to cellular nucleases. Using a PCR assay that was developed to determine the presence of full length DNAzyme, it was found that after exposure to 10% FBS for 1 hr at 37° C., full length DNAzyme could still be observed on the DNz-NAN surface (FIG. 13D). The DNAzyme was also synthesized with a terminal dye (TYE-665) and ligated to the NAN for cellular tracking. 1 μM Dye-DNz-NANs were incubated with MCF-7 cells for 4 hr and monitored for evidence of uptake using confocal microscopy (FIGS. 15A and 15B). Next, gene knockdown by the DNz-NAN was compared to that of siRNA and free DNAzymes (both delivered using lipofectamine-2000), wherein the DNz-NANs performed comparably, resulting in 60% knockdown of GATA-3 (FIG. 15C). Furthermore, it was found that the DNz-NAN showed a persistence of knockdown that continued for over 12 hrs. By 48 hr, the mRNA levels of GATA-3 showed evidence of recovery, although still at 60% relative to the untreated cells (FIG. 15D).

Figure 16:
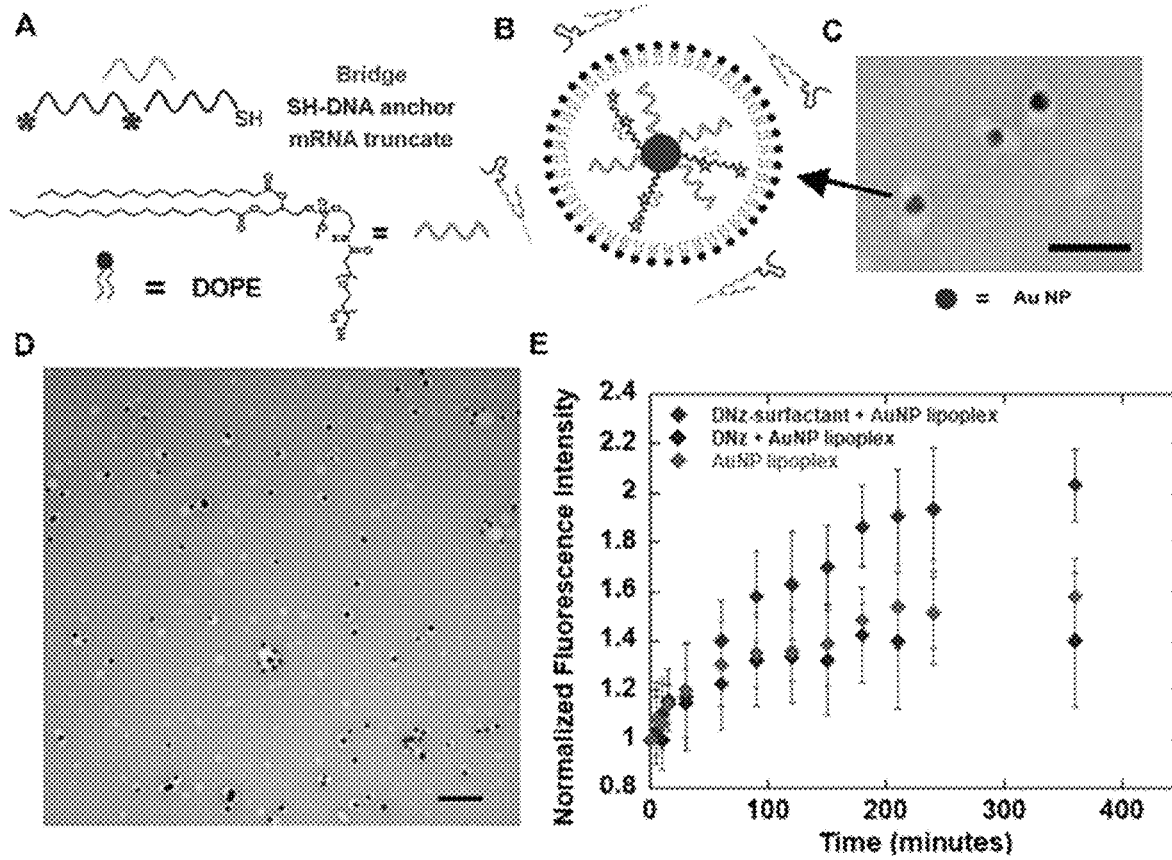
FIG. 16 illustrates mRNA cleavage by DNAzyme-surfactants on AuNP-templated lipid bilayers. (A) Assembly components of the lipid bilayer templated on a gold nanoparticle (Au NP), including thiolated DNA (purple) which is adsorbed on to the surface of the Au NP (dark gray circle) alongside a thiolated PEG DSPE lipid (gray). A fluorescently labeled mRNA truncate (purple) is hybridized to the thiolated DNA anchor using a complementary DNA bridge (light green). (B) The assembled construct shields the mRNA target from the DNz-surfactants. (C) The assembled construct is roughly 40 nm in size as shown by TEM, scale bar 50 nm. (D) TEM image showing the lipid bilayers assembled on Au NPs, scale bar 100 nm. (E) Fluorescence from the mRNA truncate within the Au NP lipoplex post incubation with either the DNAzyme, DNAzyme surfactant, or a salt solution control. Data reported is the average of three trials with accompanying standard deviation.

A synthetic lipoplex system was designed to help monitor mRNA cleavage across a lipid bilayer (FIG. 16A). This construct was built using a gold nanoparticle (Au NP) as it can support a simplified lipid bilayer system (FIG. 16B). At the Au NPs surface, both a thiolated DNA molecule and a thiolated PEG-DSPE molecule were assembled (1:2 ratio). The DNA at the surface serves as an anchoring site for the annealing of the 19mer mRNA truncate. For this assay, the same mRNA truncate that was utilized in the kinetics assay was used. Therefore, unless cleaved, the molecule should have limited fluorescence as it has both the BHQ quencher and FAM modifications. This construct was further encapsulated with DOPE, to form a bilayer around the AuNPs, a procedure previously disclosed (Shen et al. *Nanoscale*, 2016, 8, 14821-14835.) These particles were then subjected to either the free DNAzyme or DNAzyme-surfactants, and the extent of mRNA cleavage evaluated as a function of increases observed in overall fluorescence. To mimic more closely the DNz-surfactant that would results from the DNz-NANs post degradation by endosomal esterases, a modified surfactant which presented only two alkynes was synthesized, attached the DNA anchor to it, and ligated DNAzymes to the anchor to form a DNAzyme-surfactant conjugate. The results indicate that the hydrophobically modified DNAzyme can access the mRNA truncate and cleave it, whereas the DNAzyme alone appears to show limited change in signal, likely do to its inability to access the mRNA truncate (FIG. 16E). Changes in fluorescence by the free DNAzyme compared to changes in fluorescence by background salts (control sample) shows an overall minimal change in mRNA fluorescence, also indicating limited access to the mRNA target. All conditions had equal concentrations of DNAzyme.

Taken together, these results show that the multifunctional nanoparticles of the disclosure are a successful delivery system for intracellular nucleic acid delivery, and an effective gene knockdown strategy, which avoids common drawbacks such as the use of traditional cationic transfection agents and further chemical modifications. The multifunctional nanoparticles of the disclosure provide an effective nucleic acid delivery into the cell and the hydrophobic surfactant modification of the DNAzyme enables uptake and access to the mRNA target. Lastly, the delivery of the DNAzyme-NANs of the disclosure resulted in specific and persistent gene knockdown of a target gene, GATA-3, for several hours. In certain embodiments, the multifunctional nanoparticles of the disclosure may be used for co-delivery of hydrophobic drugs and oligonucleotides.

Example 6

Figure 17:
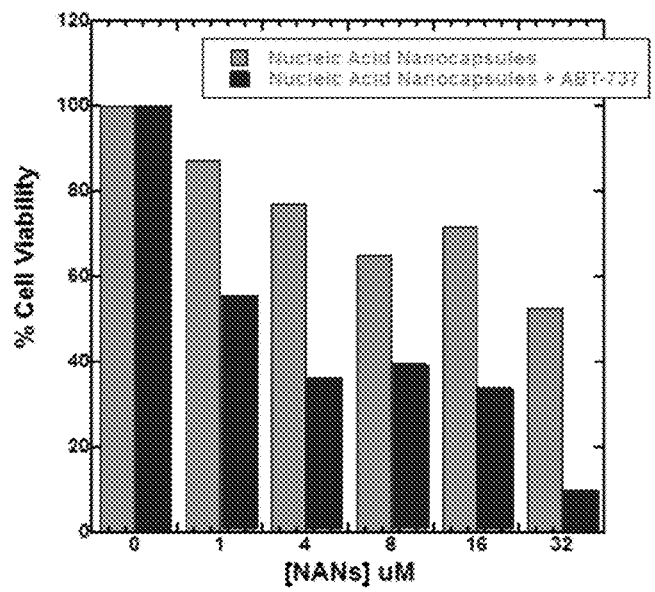
FIG. 17 illustrates HeLa cells viability when treated with unloaded NANs of Example 1 and NANs of Example 1 loaded with ABT-737 (a small molecule inhibitor of Bcl-2 family proteins).

Ester-crosslinked NANs of Example 1 were loaded with sudan II and incubated with HeLa cells. Compared to cells treated with NANs without Sudan II dye, fluorescence was observed in HeLa cells treated at 0.5 µM NANs. Next, MMT was used to evaluate cell viability. As illustrated in FIG. 17, unloaded NANs maintained ~80% cell viability up to 2 µM, above cell treatment concentrations. When loaded with ABT-737 (a small molecule inhibitor of Bcl-2 family proteins), significant cell death is observed.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A multifunctional nanoparticle comprising one or more of nucleic acid ligands covalently attached to a particle comprising non-polymeric amphiphiles,
wherein hydrophobic groups of the amphiphiles are arranged toward the particle interior, and
wherein hydrophilic groups of the amphiphiles are at the particle surface and are crosslinked through a triazole, thioether, or alkenyl sulfide group with one or more peptide linkers cleavable by one or more intracellular or extracellular release agents.

2. The multifunctional nanoparticle of claim 1, wherein the hydrophobic groups of the amphiphile comprise $C_6$-$C_{22}$ alkyl, $C_6$-$C_{22}$ alkenyl, or $C_6$-$C_{22}$ alkynyl group.

3. The multifunctional nanoparticle of claim 1, wherein the hydrophilic groups of the amphiphile comprise an ammonium group.

4. The multifunctional nanoparticle of claim 1, wherein the linker is cleavable by an enzyme.

5. The multifunctional nanoparticle of claim 1, wherein the peptide linker comprises GPLGLAGGERDG (SEQ ID NO:10), GFLG (SEQ ID NO:11), GPMGIAGQ (SEQ ID NO:12), Phe-Leu, Val-Ala, Val-Cit, Val-Lys, Val-Arg, or Phe-Lys.

6. The multifunctional nanoparticle of claim 1, wherein the linker comprises a disulfide group.

7. The multifunctional nanoparticle of claim 1, wherein the nucleic acid ligands are capable of selectively binding to a cell surface antigen.

8. The multifunctional nanoparticle of claim 1, wherein the nucleic acid ligand is capable of gene regulation, and wherein the nucleic acid is siRNA, DNAzyme, ribozyme, microRNA, or other therapeutic oligonucleotide.

9. The multifunctional nanoparticle of claim 1, wherein the nucleic acid ligand is capable of selectively binding to a protein, wherein the protein is selected from the group consisting of tumor-markers, integrins, cell surface receptors, transmembrane proteins, ion channels, membrane transport protein, enzymes, antibodies, and chimeric proteins.

10. The multifunctional nanoparticle of claim 1, wherein the nucleic acid ligand is capable of selectively binding to a carbohydrate, wherein the carbohydrate is selected from the group consisting of glycoproteins, sugar residues, and glycocalyx.

11. The multifunctional nanoparticle of claim 1, wherein the nucleic acid ligand is capable of selectively binding DNA, RNA, modified DNA, modified RNA, DNAzymes, ribozymes, mRNA, siRNA, microRNA, shRNA, and combinations thereof.

12. The multifunctional nanoparticle of claim 1, wherein the non-polymeric amphiphiles are derived from

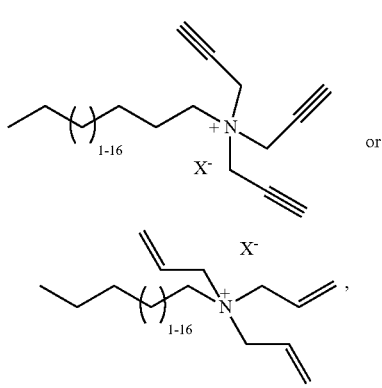

wherein X is halogen.

13. A conjugate comprising the multifunctional nanoparticle of claim 1 and at least one therapeutic agent or diagnostic agent, wherein the multifunctional nanoparticle encapsulates the therapeutic agent or diagnostic agent.

14. The conjugate of claim 13, wherein the conjugate comprises a therapeutic agent which is a hydrophobic small molecule drug selected from group consisting of an anticancer agent, an antibiotic, an antiviral, an antiparasitic agent, an anticoagulant, an analgesic agent, an anesthetic agent, an ion channel potentiator, an ion channel inhibitor, an anti-inflammatory, a metallodrug, and any combination thereof.

15. The conjugate of claim 13, wherein the conjugate comprises a diagnostic agent, which is a fluorophore, a radiolabeled nucleotide, a radioisotope, biotin, tocopherol, cholesterol, a steroid, or a electron dense tag and a metal chelator.

* * * * *